(12) United States Patent
Lovett et al.

(10) Patent No.: US 8,512,220 B2
(45) Date of Patent: *Aug. 20, 2013

(54) RATE SMOOTHING CONTROL

(75) Inventors: Eric G. Lovett, Mendota Heights, MN (US); Mark Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1597 days.

This patent is subject to a terminal disclaimer.

(21) Appl. No.: 11/759,394

(22) Filed: Jun. 7, 2007

(65) Prior Publication Data

US 2007/0233201 A1    Oct. 4, 2007

Related U.S. Application Data

(60) Division of application No. 10/017,800, filed on Dec. 12, 2001, now Pat. No. 7,239,914, which is a continuation-in-part of application No. 09/579,951, filed on May 26, 2000, now Pat. No. 6,501,987.

(51) Int. Cl.
*A61N 1/365* (2006.01)

(52) U.S. Cl.
USPC .......................................................... 600/17

(58) Field of Classification Search
USPC .................................................. 607/9, 17–19
See application file for complete search history.

(56) References Cited

U.S. PATENT DOCUMENTS

| | | |
|---|---|---|
| 3,857,399 A | 12/1974 | Zacouto |
| 4,030,510 A | 6/1977 | Bowers |
| 4,059,116 A | 11/1977 | Adams |
| 4,163,451 A | 8/1979 | Lesnick et al. |
| 4,208,008 A | 6/1980 | Smith |
| RE30,387 E | 8/1980 | Denniston, III et al. |
| 4,432,360 A | 2/1984 | Mumford et al. |
| 4,503,857 A | 3/1985 | Boute et al. |

(Continued)

FOREIGN PATENT DOCUMENTS

| | | |
|---|---|---|
| EP | 0033418 | 8/1981 |
| EP | 0360412 | 3/1990 |

(Continued)

OTHER PUBLICATIONS

U.S. Appl. No. 10/017,800, Advisory Action mailed Apr. 21, 2005, 3 pgs.

(Continued)

*Primary Examiner* — George Evanisko

(74) *Attorney, Agent, or Firm* — Schwegman Lundberg & Woessner, P.A.

(57) ABSTRACT

A rate smoothing function used in implantable pulse generators uses detected triggering events, which cause the rate smoothing function to be activated or deactivated, and detected parameter adjusting events, which cause parameter(s) of the rate smoothing function to be changed. In one example, the activation/deactivation and/or change to the parameters of the rate smoothing function are temporary, and the pre-event state of the rate smoothing function is set to a post-adjusting state, such as after a first time interval. Rate smoothing may be selected, activated or deactivated, or adjusted based on a cardiac signal state, or based on an activity or other physiological sensor signal. The adjusted rate smoothing parameters may include an up-smoothing percentage to limit a speed of pacing rate increase and a down-smoothing percentage to limit a speed of pacing rate drop.

21 Claims, 13 Drawing Sheets

(56) References Cited

U.S. PATENT DOCUMENTS

| | | |
|---|---|---|
| 4,556,063 A | 12/1985 | Thompson et al. |
| 4,562,841 A * | 1/1986 | Brockway et al. .............. 607/29 |
| 4,596,255 A | 6/1986 | Snell et al. |
| 4,791,936 A | 12/1988 | Snell et al. |
| 4,809,697 A | 3/1989 | Causey, III et al. |
| 4,830,006 A | 5/1989 | Haluska et al. |
| 4,869,252 A | 9/1989 | Gilli |
| 4,890,617 A | 1/1990 | Markowitz et al. |
| 4,905,697 A | 3/1990 | Heggs et al. |
| 4,917,115 A | 4/1990 | Flammang et al. |
| 4,920,965 A | 5/1990 | Funke et al. |
| 4,928,688 A | 5/1990 | Mower |
| 4,940,054 A | 7/1990 | Grevis et al. |
| 4,941,471 A | 7/1990 | Mehra |
| 4,944,298 A | 7/1990 | Sholder |
| 4,944,928 A | 7/1990 | Grill et al. |
| 4,945,909 A | 8/1990 | Fearnot et al. |
| 4,972,834 A | 11/1990 | Begemann et al. |
| 4,998,974 A | 3/1991 | Aker |
| 5,012,814 A | 5/1991 | Mills et al. |
| 5,042,480 A | 8/1991 | Hedin et al. |
| 5,085,215 A | 2/1992 | Nappholz et al. |
| 5,101,824 A | 4/1992 | Lekholm |
| 5,107,850 A | 4/1992 | Olive |
| 5,127,404 A | 7/1992 | Wyborny et al. |
| 5,129,394 A | 7/1992 | Mehra |
| 5,139,020 A | 8/1992 | Koestner et al. |
| 5,144,949 A | 9/1992 | Olson |
| 5,156,147 A | 10/1992 | Warren et al. |
| 5,156,154 A | 10/1992 | Valenta, Jr. et al. |
| 5,179,949 A | 1/1993 | Chirife |
| 5,183,040 A | 2/1993 | Nappholz et al. |
| 5,184,614 A | 2/1993 | Collins et al. |
| 5,188,106 A | 2/1993 | Nappholz et al. |
| 5,193,535 A | 3/1993 | Bardy et al. |
| 5,193,550 A | 3/1993 | Duffin |
| 5,197,467 A | 3/1993 | Steinhaus et al. |
| 5,207,219 A | 5/1993 | Adams et al. |
| 5,271,395 A | 12/1993 | Wahlstrand et al. |
| 5,282,836 A | 2/1994 | Kreyenhagen et al. |
| 5,284,491 A | 2/1994 | Sutton et al. |
| 5,292,339 A | 3/1994 | Stephens et al. |
| 5,292,341 A | 3/1994 | Snell |
| 5,311,874 A | 5/1994 | Baumann et al. |
| 5,312,452 A | 5/1994 | Salo |
| 5,331,966 A | 7/1994 | Bennett et al. |
| 5,334,220 A | 8/1994 | Sholder |
| 5,350,409 A | 9/1994 | Stoop et al. |
| 5,356,425 A | 10/1994 | Bardy et al. |
| 5,360,437 A | 11/1994 | Thompson |
| 5,365,932 A | 11/1994 | Greenhut |
| 5,372,607 A | 12/1994 | Stone et al. |
| 5,376,106 A | 12/1994 | Stahmann et al. |
| 5,379,776 A | 1/1995 | Murphy et al. |
| 5,383,910 A | 1/1995 | den Dulk |
| 5,387,229 A | 2/1995 | Poore |
| 5,391,189 A | 2/1995 | van Krieken et al. |
| 5,395,373 A | 3/1995 | Ayers |
| 5,395,397 A | 3/1995 | Lindgren et al. |
| 5,400,796 A | 3/1995 | Wecke |
| 5,411,524 A | 5/1995 | Rahul |
| 5,411,531 A | 5/1995 | Hill et al. |
| 5,417,714 A | 5/1995 | Levine et al. |
| 5,423,869 A | 6/1995 | Poore et al. |
| 5,431,691 A | 7/1995 | Snell et al. |
| 5,437,285 A | 8/1995 | Verrier et al. |
| 5,462,060 A | 10/1995 | Jacobson et al. |
| 5,474,574 A | 12/1995 | Payne et al. |
| 5,480,413 A | 1/1996 | Greenhut et al. |
| 5,486,198 A | 1/1996 | Ayers et al. |
| 5,487,752 A | 1/1996 | Salo et al. |
| 5,507,782 A | 4/1996 | Kieval et al. |
| 5,507,784 A | 4/1996 | Hill et al. |
| 5,514,163 A | 5/1996 | Markowitz et al. |
| 5,522,850 A | 6/1996 | Yomtov et al. |
| 5,522,859 A | 6/1996 | Stroebel et al. |
| 5,523,942 A | 6/1996 | Tyler et al. |
| 5,527,347 A | 6/1996 | Shelton et al. |
| 5,534,016 A | 7/1996 | Boute |
| 5,540,232 A | 7/1996 | Laney et al. |
| 5,540,727 A | 7/1996 | Tockman et al. |
| 5,545,182 A | 8/1996 | Stotts et al. |
| 5,545,186 A | 8/1996 | Olson et al. |
| 5,549,649 A | 8/1996 | Florio et al. |
| 5,549,654 A | 8/1996 | Powell |
| 5,554,174 A | 9/1996 | Causey, III |
| 5,560,369 A | 10/1996 | McClure et al. |
| 5,560,370 A | 10/1996 | Verrier et al. |
| 5,562,711 A | 10/1996 | Yerich et al. |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. |
| 5,607,460 A | 3/1997 | Kroll et al. |
| 5,613,495 A | 3/1997 | Mills et al. |
| 5,620,471 A | 4/1997 | Duncan |
| 5,620,473 A | 4/1997 | Poore |
| 5,622,178 A | 4/1997 | Gilham |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,683,429 A | 11/1997 | Mehra |
| 5,690,689 A | 11/1997 | Sholder |
| 5,700,283 A | 12/1997 | Salo |
| 5,702,424 A * | 12/1997 | Legay et al. ...................... 607/9 |
| 5,713,929 A | 2/1998 | Hess et al. |
| 5,713,930 A | 2/1998 | van der Veen et al. |
| 5,713,932 A | 2/1998 | Gillberg et al. |
| 5,716,382 A | 2/1998 | Snell |
| 5,716,383 A | 2/1998 | Kieval et al. |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,725,561 A * | 3/1998 | Stroebel et al. ................... 607/9 |
| 5,730,141 A | 3/1998 | Fain et al. |
| 5,730,142 A | 3/1998 | Sun et al. |
| 5,738,096 A | 4/1998 | Ben-Haim |
| 5,741,304 A | 4/1998 | Patwardhan et al. |
| 5,741,308 A | 4/1998 | Sholder |
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,776,164 A | 7/1998 | Ripart |
| 5,776,167 A | 7/1998 | Levine et al. |
| 5,782,887 A | 7/1998 | van Krieken et al. |
| 5,788,717 A | 8/1998 | Mann et al. |
| 5,792,193 A | 8/1998 | Stoop |
| 5,800,464 A | 9/1998 | Kieval |
| 5,800,471 A | 9/1998 | Baumann |
| 5,814,077 A | 9/1998 | Sholder et al. |
| 5,814,081 A | 9/1998 | Ayers et al. |
| 5,814,085 A | 9/1998 | Hill |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,846,263 A | 12/1998 | Peterson et al. |
| 5,853,426 A | 12/1998 | Shieh |
| 5,855,593 A | 1/1999 | Olson et al. |
| 5,861,007 A | 1/1999 | Hess et al. |
| 5,865,838 A | 2/1999 | Obel et al. |
| 5,873,895 A | 2/1999 | Sholder et al. |
| 5,873,897 A | 2/1999 | Armstrong et al. |
| 5,891,178 A | 4/1999 | Mann et al. |

| | | |
|---|---|---|
| 5,893,882 A | 4/1999 | Peterson et al. |
| 5,897,575 A | 4/1999 | Wickham |
| 5,902,324 A | 5/1999 | Thompson et al. |
| 5,928,271 A | 7/1999 | Hess et al. |
| 5,931,857 A | 8/1999 | Prieve et al. |
| 5,935,081 A | 8/1999 | Kadhiresan |
| 5,944,744 A | 8/1999 | Paul et al. |
| 5,951,592 A | 9/1999 | Murphy |
| 5,968,079 A | 10/1999 | Warman et al. |
| 5,974,341 A | 10/1999 | Er et al. |
| 5,978,707 A | 11/1999 | Krig et al. |
| 5,978,710 A | 11/1999 | Prutchi et al. |
| 5,983,138 A | 11/1999 | Kramer |
| 5,987,354 A | 11/1999 | Cooper et al. |
| 5,987,356 A | 11/1999 | DeGroot |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 6,026,320 A | 2/2000 | Carlson et al. |
| 6,041,251 A | 3/2000 | Kim et al. |
| 6,044,298 A | 3/2000 | Salo et al. |
| 6,047,210 A | 4/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,058,328 A | 5/2000 | Levine et al. |
| 6,070,101 A | 5/2000 | Struble et al. |
| 6,081,745 A | 6/2000 | Mehra |
| 6,081,746 A | 6/2000 | Pendekanti et al. |
| 6,081,747 A | 6/2000 | Levine et al. |
| 6,081,748 A | 6/2000 | Struble et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,096,064 A | 8/2000 | Routh |
| 6,122,545 A | 9/2000 | Struble et al. |
| 6,128,529 A | 10/2000 | Esler |
| 6,129,745 A | 10/2000 | Sun et al. |
| 6,134,469 A | 10/2000 | Wietholt |
| 6,151,524 A | 11/2000 | Krig et al. |
| 6,223,072 B1 | 4/2001 | Mika et al. |
| 6,246,909 B1 | 6/2001 | Ekwall |
| 6,249,699 B1 | 6/2001 | Kim |
| 6,256,534 B1 | 7/2001 | Dahl |
| 6,263,242 B1 | 7/2001 | Mika et al. |
| 6,266,554 B1 | 7/2001 | Hsu et al. |
| 6,272,380 B1 | 8/2001 | Warman et al. |
| 6,285,907 B1 | 9/2001 | Kramer et al. |
| 6,292,693 B1 | 9/2001 | Darvish et al. |
| 6,317,632 B1 | 11/2001 | Krig et al. |
| 6,351,669 B1 | 2/2002 | Hartley et al. |
| 6,353,759 B1 | 3/2002 | Hartley et al. |
| 6,353,761 B1 | 3/2002 | Conley et al. |
| 6,408,209 B1 | 6/2002 | Bouhour et al. |
| 6,411,847 B1 | 6/2002 | Mower |
| 6,411,848 B2 | 6/2002 | Kramer et al. |
| 6,424,865 B1 | 7/2002 | Ding |
| 6,430,438 B1 | 8/2002 | Chen et al. |
| 6,434,424 B1 | 8/2002 | Igel et al. |
| 6,438,410 B2 | 8/2002 | Hsu et al. |
| 6,501,987 B1 * | 12/2002 | Lovett et al. ............ 607/9 |
| 6,501,988 B2 | 12/2002 | Kramer et al. |
| 6,512,951 B1 | 1/2003 | Marcovecchio et al. |
| 6,522,925 B1 | 2/2003 | Gilkerson et al. |
| RE38,119 E | 5/2003 | Mower |
| 6,687,541 B2 | 2/2004 | Marcovecchio et al. |
| 6,847,842 B1 | 1/2005 | Rodenhiser et al. |
| 6,957,100 B2 | 10/2005 | Vanderlinde et al. |
| 6,988,002 B2 | 1/2006 | Kramer et al. |
| 7,039,461 B1 | 5/2006 | Lovett |
| 7,047,066 B2 | 5/2006 | Vanderlinde et al. |
| 7,062,325 B1 | 6/2006 | Krig et al. |
| 7,069,077 B2 * | 6/2006 | Lovett et al. ............ 607/17 |
| 7,142,915 B2 | 11/2006 | Kramer et al. |
| 7,142,918 B2 | 11/2006 | Stahmann et al. |
| 7,212,860 B2 | 5/2007 | Stahmann et al. |
| 7,239,914 B2 | 7/2007 | Lovett et al. |
| 7,460,908 B2 | 12/2008 | Krig et al. |
| 7,680,530 B2 | 3/2010 | Vanderlinde et al. |
| 7,742,814 B2 | 6/2010 | Lovett |
| 2002/0062139 A1 | 5/2002 | Ding |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0120298 A1 | 8/2002 | Kramer et al. |
| 2003/0004551 A1 | 1/2003 | Chen et al. |
| 2003/0069610 A1 | 4/2003 | Kramer et al. |
| 2003/0078630 A1 | 4/2003 | Lovett et al. |
| 2003/0233131 A1 | 12/2003 | Kramer et al. |
| 2004/0010295 A1 | 1/2004 | Kramer et al. |
| 2004/0172076 A1 | 9/2004 | Stahmann et al. |
| 2004/0215259 A1 | 10/2004 | Krig et al. |
| 2007/0135853 A1 | 6/2007 | Kramer et al. |
| 2007/0288062 A1 | 12/2007 | Stahman et al. |
| 2009/0076563 A1 | 3/2009 | Krig et al. |
| 2010/0145407 A1 | 6/2010 | Vanderlinde et al. |
| 2010/0222836 A1 | 9/2010 | Jarverud |
| 2010/0249866 A1 | 9/2010 | Lovett |

FOREIGN PATENT DOCUMENTS

| | | |
|---|---|---|
| EP | 0401962 | 12/1990 |
| EP | 0597459 | 5/1994 |
| EP | 0617980 | 10/1994 |
| EP | 0748638 | 12/1996 |
| JP | 7-72910 A | 3/1995 |
| WO | WO-93/02746 | 2/1993 |
| WO | WO-95/09029 | 4/1995 |
| WO | WO-97/11745 | 4/1997 |
| WO | WO-9739798 | 10/1997 |
| WO | WO-98/48891 | 11/1998 |
| WO | WO-00/71200 | 11/2000 |
| WO | WO-00/71203 | 11/2000 |
| WO | WO-0071202 | 11/2000 |

OTHER PUBLICATIONS

U.S. Appl. No. 10/017,800, Advisory Action mailed Apr. 27, 2006, 4 pgs.

U.S. Appl. No. 10/017,800, Response filed Apr. 24, 2006 to Final Office Action mailed Feb. 24, 2006, 13 pgs.

U.S. Appl. No. 10/017,800, Appeal Brief filed Jul. 10, 2006, 23 pgs.

U.S. Appl. No. 10/017,800, Final Office Action mailed Feb. 8, 2005, 8 pgs.

U.S. Appl. No. 10/017,800, Final Office Action mailed Feb. 24, 2006, 8 pgs.

U.S. Appl. No. 10/017,800, Final Office Action mailed Nov. 15, 2005, 8 pgs.

U.S. Appl. No. 10/017,800, Non-Final Office Action mailed Jul. 5, 2005, 10 pgs.

U.S. Appl. No. 10/017,800, Non-Final Office Action mailed Aug. 24, 2004, 6 pgs.

U.S. Appl. No. 10/017,800, Notice mailed Jul. 25, 2006, 3 pgs.

U.S. Appl. No. 10/017,800, Notice of Allowance mailed Feb. 20, 2007, 6 pgs.

U.S. Appl. No. 10/017,800, Notice of Allowance mailed Oct. 27, 2006, 6 pgs.

U.S. Appl. No. 10/017,800, Preliminary Amendment filed Jan. 12, 2007, 4 pgs.

U.S. Appl. No. 10/017,800, Response filed Jan. 13, 2006 to Final Ofice Ation mailed Nov. 15, 2005, 14 pgs.

U.S. Appl. No. 10/017,800, Response filed Apr. 5, 2005 to Final Office Action mailed Feb. 8, 2005, 14 pgs.

U.S. Appl. No. 10/017,800, Response filed Aug. 2, 2006 to Notice of Non-Compliant Appeal Brief mailed Jul. 25, 2006, 21 pgs.

U.S. Appl. No. 10/017,800, Response filed Sep. 6, 2005 to Non Final Office Action mailed Jul. 5, 2005, 14 pgs.

U.S. Appl. No. 10/017,800, Response filed Nov. 23, 2004 to Non-Final Office Action mailed Aug. 24, 2004, 15 pgs.

*Metrix Model 3020 Implantable Atrial Defibrillator*, Physician's Manual, InControl, Inc., Redmond, WA,(1998),pp. 4-24-4-27.

"French CNH Equipment Approvals", *Clinica*, 417, p. 9, (Sep. 5, 1990),3 pages.

"Pacemaker System Guide for PULSAR MAX II; Mulitprogrammable Pacemakers", Product brochure published by Guidant Corporation,(Apr. 18, 1999),pp. 6-48 and 6-49.
"Pacemaker System Guide for PULSAR MAX II; Multiprogrammable Pacemakers", Product brochure published by Guidant Corporation,(Apr. 18, 1999),p. 6-39-6-51.
"Rate-Adaptive Devices Impact Pacemaker Market", *Clinica*, 467, D. 16, (Sep. 11, 1991),6 pages.
"Vitatron Medical Harmony Automatic Dual Chamber Pacemaker Product Information and Programming Guide", Viatron Medical, 22 p., (Date Unknown), Harmony Dual Chamber mentioned in publication *Clinica*, 467, p. 16, Sep. 11, 1991, "Rate Devices Impact Pacemaker Market", also mentioned in *Clinica*, 417, p. 9, Sep. 5, 1990 "French CNH Equipment Approvals"., Product Brochure published by Vitatron Medical,22 pgs.
Ayers, Gregory M., et al., "Ventricular Proarrhythmic Effects of Ventricular Cycle Length and Shock Strength in a Sheep Model of Transvenous Atrial Defibrillation", *Circulation*, 89 (1), (Jan. 1994),413-422.
Blommaert, D. , et al., "Effective Prevention of Atrial Fibrillation by Continuous Atrial Overdrive Pacing After Coronary Artery Bypass Surgery", *JACC*, vol. 35, No. 6, (May 2000),pp. 1411-1415.
Buhr, Trina A., et al., "Novel Pacemaker Algorithm Diminishes Short-Coupled Ventricular Beats in Atrial Fibrillation", *PACE*, vol. 24, Part II, (Apr. 2001),729.
Campbell, R. M., et al., "Atrial Overdrive Pacing for Conversion of Atrial Flutter in Children", *Pediatrics*, 75(4), (Apr. 1985),730-736.
Clark, David M., et al., "Hemodynamic Effects of an Irregular Sequence of Ventricular Cycle Lengths During Atrial Fibrillation", *JACC*, vol. 30, No. 4, (Oct. 1997),1039-1045.
Duckers, H. J., et al., "Effective use of a novel rate-smoothing algorithm in atrial fibrillation by ventricular pacing", *European Heart Journal*, 18, (1997),pp. 1951-1955.
Fahy, G. J., et al., "Pacing Strategies to Prevent Atrial Fibrillation", *Atrial Fibrillation*, 14 (4), (Nov. 1996),pp. 591-596.
Fromer, M. , et al., "Algorithm for the Prevention of Ventricular Tachycardia Onset: The Prevent Study", *The American Journal of Cardiology*, 83 (5B), (Mar. 11, 1999),pp. 45D-47D.
Garrigue, S. , et al., "Prevention of Atrial Arrhythmias during DDD Pacing by Atrial Overdrive", *PACE*, vol. 21, (Sep. 1998),pp. 1751-1759.
Greenhut, S. , et al., "Effectiveness of a Ventricular Rate Stabilization Algorithm During Atrial Fibrillation in Dogs", *Pace Abstract*, Abstract No. 60,(1996),1 p.
Guidant, "CONTAK TR CHFD Model 1241", *System Guide*, Congestive Heart Failure Device,(1999),1-191.
Heuer, H. , et al., "Dynamic Dual-Chamber Overdrive Pacing with an Implantable Pacemaker System: A New Method or Terminating Slow Ventricular Tachycardia", *Zeitschrift fur Kardiologie*, 75, German Translation by the Ralph McElroy Translation Company, Austin, TX,(1986),6 pages.
Heuer, H. , et al., "Dynamische Zweikammer-Overdrive-Stimulation mit einem implantierbaren Schrittmachersystem als neue Methode zur Beendigung Langsamer ventrikularer Tachykardien", *Z Kardiol*; 75, Includes English translation (5 pgs.),(1986),pp. 673-675.
Jenkins, "Diagnosis of Atrial Fibrillation Using Electrogram from Chronic Leads: Evaluation of Computer Algorithm", *PACE*, 11, (1988),pp. 622-631.
Jung, J. , et al., "Discrimination of Sinus Rhythm, Atrial Flutter, and Atrial Fibrillation Using Bipolar Endocardial Signals", *Journal of Cardiovascular Electrophysiology*, 9 (7), (Jul. 1998),pp. 689-695.
Krig, D. B., et al., "Method and Apparatus for Treating Irregular Ventricular Contractions Such as During Atrial Arrhythmia", U.S. Appl. No. 09/316,515, filed May 21, 1999, 57 pages.
Krig, David B., "Method and Apparatus for Treating Irregular Ventricular Contractions Such as During Atrial Arrhythmia", U.S. Appl. No. 10/643,590, filed Aug. 19, 2003, 45 pgs.
Krig, David B., "Method and Apparatus for Treating Irregular Ventricular Contractions Such as During Atrial Arrhythmia", U.S. Appl. No. 10/852,602, filed May 24, 2004, 60 pgs.
Lau, Chu-Pak , et al., "Efficacy of Ventricular Rate Stabilization by Right Ventricular Pacing During Atrial Fibrillation", *PACE*, vol. 21, (Mar. 1998),542-548.
Lovett, Eric , "Cardiac Pacing System for Prevention of Ventricular Fibrillation and Ventricular Tachycardia Episode", U.S. Appl. No. 09/569,295, filed May 13, 2000, 71 pgs.
Medtronic, "INSYNC Device Model 8040", *Device Reference Guide*, (Aug. 2001),1-276.
Medtronic, "INSYNC III Device Model 8042", *Device Programming Guide*, INSYNC III Device Model 8042, Vision Programmer Software Model 9981,(2000),1-260.
Medtronic, "INSYNC Model 8040 Device Programming Guide", *Device Programming Guide*, Device Model 8040 & Programmer Software Model 9980,(2001),1-204.
Mehra, R. , et al., "Prevention of Atrial Fibrillation/Flutter by Pacing Techniques", *Interventional Electrophysiology, Second Edition*, Chapter 34, Futura Publishing Company, Inc.,(1996),pp. 521-540.
Morris, et al., "Intracardiac Electrogram Transformation: Morphometric Implications for Implantable Devices", *Journal of Electrocardiology, 29 Supplement*, (1996),pp. 124-129.
Mower, Morton, U.S. Patent Office Patent Application Information Retrieval (PAIR) search results for U.S. Appl. No. 10/214,474, filed Aug. 8, 2002, entitled "*Method and Apparatus for Treating Hemodynamic Disfunction*", 3.
Murgatroyd, F. D., et al., "A New Pacing Algorithm for Overdrive Suppression of Atrial Fibrillation", *Pace*, vol. 17., (Nov. 1994, Part),pp. 1966-1973.
Schuller, et al., "Far Field R-Wave Sensing—An Old Problem Repeating", *PACE*, 19, Part II, NASPE Abstract No. 264,(1996),p. 631.
Seim, G. , et al., "Classification of Atrial Flutter and Atrial Fibrillation Using an Atrial Dispersion Index (ADI)", *Guidant CRM Therapy Research Peer Review Report Revision* 2.0, (Jan. 6, 1999),27 p.
Stahmann, Jeffrey E., et al., "Apparatus and Method for Pacing Mode Switching During Atrial Tachyarrhythmias", U.S. Appl. No. 10/713,556, filed Nov. 13, 2003, 26 pgs.
Stephany, et al., "Real-Time Estimation of Magnitude-Square Coherence for Use in Implantable Devices", *IEEE Computers in Cardiology*, (1992),pp. 375-378.
Sutton, R. , "Pacing in Atrial Arrhythmias", *PACE*, vol. 13, (Dec. 1990, Part),pp. 1823-1827.
Swiryn, S. , et al., "Detection of Atrial Fibrillation by Pacemakers and Antiarrhythmic Devices", *Nonpharmacological Management of Atrial Fibrillation*, Chapter 21, Futura Publishing Co, Inc. Armonk, NY,(1997),pp. 309-318.
Vanderlinde, Scott , et al., "Method and System for Display of Cardiac Event Intervals in a Resynchronization Pacemaker", U.S. Appl. No. 10/792,663, filed Mar. 3, 2004, 23 pgs.
Wittkampf, Fred H., et al., "Effect of Right Ventricular Pacing on Ventricular Rhythm During Atrial Fibrillation", *JACC* , vol. 11, No. 3, (Mar. 1988),539-545.
Wittkampf, F.H.M. , et al., "Rate Stabilization by Right Ventricular Patching in Patients with Atrial Fibrillation", *Pace*, 9, (Nov.-Dec. 1986),1147-1153.
Zhu, D. W., "Electrophysiology, Pacing and Arrhythmia—Pacing Therapy for Atrial Tachyarrhythmias", *Clinical Cardiology*, 19(9), (1996),737-742.
Zhu, D. , et al., "Pacing therapy for atrial tachyarrhythmias", *Clin. Cardiol.*, 19(9), (Sep. 1996),737-742
"U.S. Appl. No. 10/107,800, Supplemental Amendment & Response filed May, 9, 2005 to Advisory Action mailed Apr. 21, 2005 and Final Office Action mailed Feb. 8, 2005", 14 pgs.

* cited by examiner

| PREDETERMINED STATE 1300 | PREDETERMINED RATE SMOOTHING ALGORITHM 1320 |
|---|---|
| #1 | A |
| #2 | B |
| #3 | C |
| #4 | D |
| #5 | E |

Fig.13

| PREDETERMINED STATE 1300 | UP-SMOOTHING PERCENTAGE 1450 | DOWN-SMOOTHING PERCENTAGE 1460 |
|---|---|---|
| #1 | 15% | 15% |
| #2 | 10% | 15% |
| #3 | 15% | 10% |
| #4 | 0% | 15% |
| #5 | 15% | 0% |

Fig.14

RATE SMOOTHING CONTROL

CROSS-REFERENCE TO RELATED APPLICATIONS

This application is a division of U.S. patent application Ser. No. 10/017,800, filed on Dec. 12, 2001, now issued as U.S. Pat. No. 7,239,914, which is a continuation-in-part of U.S. patent application Ser. No. 09/579,951, filed on May 26, 2000, now issued as U.S. Pat. No. 6,501,987, and is related to U.S. patent application Ser. No. 09/570,091, filed May 13, 2000, now abandoned, each of which is incorporated herein by reference in its entirety.

TECHNICAL FIELD

The present invention relates to pulse generators and in particular to implantable pulse generators that control pacing functions based on sensed events.

BACKGROUND

The cardiac pacemaker in its simplest form is an electrical circuit in which a battery provides electricity that travels through a conducting wire through the myocardium, stimulating the heart to beat ("capturing" the heart), and back to the battery, thus completing the circuit. Implantable cardiac pacemakers have been in existence since the later 1950's, although external pacemakers were known even earlier. Since that time great strides have been made in improving upon the leads and the pulse generators that together comprise the pacemaker. In particular, the pulse generator circuitry has evolved from discrete components to semi-custom integrated circuits, which are now fabricated from complimentary metal oxide semi-conductor (CMOS) technology.

As cardiac pacemakers have evolved they have been designed to provide increases in the heart rate for periods when the patient is experiencing physiological stress. These "rate-modulating" pacemakers help the patient adapt to physiological stress with an increase in heart rate, even if the patient's intrinsic heart rate would not allow this to occur. The development of dual-chamber pacemakers has allowed the patient to increase their heart rate if he or she is in sinus rhythm.

The rate-modulated pacemaker has three major components. The first is an indicator, such as for activity, body temperature, or respiratory rate, that provides an approximate measurement of metabolic needs. The second is a sensor that can measure the indicator chosen, such as measurement of body temperature or respiratory rate. The third is a rate controlled algorithm that is in the software of the pacemaker and modulates the pacemaker rate as the sensors send signals to the pacemaker.

As the sensors indicate greater metabolic need, the pacing rate is increased. The rate at which the pacing rate changes, however, is bounded and controlled by a feature called rate smoothing. Rate smoothing is a gradual slowing or speeding of the pacemaker rate based on a percentage of a preceding cardiac interval. This is a mechanism programmed into such types of pacemakers to reduce or to smooth abrupt changes in paced rate, especially at the upper rate limit of dual chamber pacemakers. Conversely, if a patient were to develop an ectopic atrial tachycardia, this programmed feature would cause a gradual increase in rate rather than an abrupt increase in rate.

Rate smoothing may, however, unnecessarily limit a heart rate change under some circumstances. For example, when an individual needs rapid cardiac output in a short time, such as in a stressful situation, rate smoothing may prevent the heart rate from rising rapidly enough to keep up with the individual's cardiac demands. Similarly, once the stressful situation has passed, the individual's pacing rate will decrease under the constraints imposed by the rate smoothing algorithm. Furthermore, the present inventors have also recognized that rate smoothing may interfere with arrhythmia prevention and treatment by limiting a change in heart rate that is needed to prevent or treat the arrhythmia. Thus, there exists an unmet need in the art for more flexible rate smoothing.

SUMMARY

The present invention provides a system and method for controlling a rate smoothing system in a pulse generating system. In one embodiment, the rate smoothing system is either activated or deactivated (turned on or turned off) when a triggering event is detected. In an alternative embodiment, when a parameter adjusting events is detected parameters of the rate smoothing system are adjusted (e.g., changed). Under either situation (turning on/off or adjustment of parameters) the changes to the rate smoothing system/function are temporary. In one embodiment, the duration of the changes is over a first time interval, after which the rate smoothing system is either set to the original pre-event state or to a state in which one or more of the original parameter values/settings have been changed from the original pre-event state. By allowing selected events to temporarily activate/deactivate or change parameter settings for a rate smoothing system, greater flexibility in treating a patient's cardiac conditions is achieved as compared to allowing the rate smoothing function to continuously operate. The present subject matter can be used with rate smoothing systems applied to either ventricular pacing or atrial pacing.

In one embodiment, the present system provides monitoring for a trigger signal a parameter adjusting event or both. In one embodiment, the system uses a signal input system, where the signal input system is adapted to detect a signal. Control circuitry coupled to the signal input system receives the signal from the signal input system. In one embodiment, a trigger event detector in the control circuitry receives the signal and analyzes the signal for the occurrence of the trigger event. The trigger event detector is further coupled to a rate smoothing module. In one embodiment, the rate smoothing module executes and controls the rate smoothing algorithm. When the triggering event is detected, the rate smoothing module is then either activated to provide rate smoothing or deactivated to stop rate smoothing, depending upon the state of the module prior to the triggering event. Once the rate smoothing system is activated or deactivated, a timer is used to time a first interval. After the first interval expires, the rate smoothing system is then reset, or restored, to its state prior to the trigger signal. Alternatively, after the first interval expires, the rate smoothing system changes one or more of the original parameter values/settings (i.e., pre-trigger signal parameter state or pre-parameter adjusting event parameter state) to provide a new parameter state. The new parameter state is then used in the rate smoothing system until a subsequent trigger signal and/or parameters adjusting event is detected. A new parameter state can be created after each trigger signal and/or parameters adjusting event (e.g., a sequence of changes to the parameter values and/or settings for the rate smoothing system).

In an alternative embodiment, a parameter adjustment event detector coupled to the control circuitry receives the signal from the signal input system. In one embodiment, the parameter adjustment event detector receives a signal and analyzes the signal for the occurrence of a parameter adjustment event in the signal. When the parameter adjustment event is detected, the rate smoothing module activates and/or adjusts rate smoothing parameters. In one embodiment, the parameters adjusted are a percent limiting a change in pacing rate (for either up or down rate smoothing).

Any number of detected events are used as either triggering events or parameter adjustment events. In one example, a triggering event or a parameter adjustment event is detected in a patient activity signal, such as can be sensed by using an activity monitor, such as an accelerometer or a minute ventilation system. In this example, an activity signal is monitored from an activity sensor. The triggering event or parameter adjustment event is then detected when the patient's activity level exceeds a first predetermined value. In an additional example, the activity signal is a heart rate acceleration, where the triggering event or parameter adjustment event is deemed detected when a change in heart rate exceeds the first predetermined value.

In an additional embodiment, a triggering event or a parameter adjustment event is found in a monitored cardiac signal. In one example, monitoring for the triggering event or parameter adjustment event includes monitoring a cardiac signal, where the cardiac signal includes indications of ventricular contractions. The cardiac signal is analyzed for the occurrence of premature ventricular contractions (PVC). When one or more PVC occur, the triggering event or parameter adjustment event is deemed to have been detected. Alternatively, a pattern of cycle lengths in the cardiac signal is used as a triggering event or a parameter adjustment event. For example, a detected short-long-short cycle length sequence from a cardiac signal may be used as a triggering event or parameter adjustment event. Alternatively, the triggering event or parameter adjustment event occurs when a cardiac rate exceeds a rate threshold. In an additional embodiment, the triggering event or parameter adjustment event occurs after an arrhythmic episode.

In an alternative embodiment, triggering events or parameter adjustment events occur at selected times within a time interval. In one example, monitoring for the triggering event or parameter adjustment events includes monitoring a time interval, such as the time of the day, week, month, year, or an event, such as a season of the year. The triggering event or parameter adjustment event is then detected at a first time in the time interval, as either programmed by the physician or set based on the implantable system's analysis of one or more detected signals. Alternatively, the triggering event or parameter adjustment event occurs when a pacemaker mode is changed. In one example, an implantable system provides and/or adjusts a rate smoothing system based on whether a state of a monitored signal matches a predetermined state. In one example, the monitored signal is a cardiac signal sensed with electrodes in or about the heart. The cardiac signal matches the predetermined state if a heart rate exceeds a predetermined threshold or, alternatively, falls within a predetermined range of heart rates. In another example, the cardiac rhythm is compared to a predetermined cardiac rhythm state. In yet another example, a patient activity signal (e.g., sensed by an accelerometer or a respiration sensor to represent a patient's metabolic need for a particular range of heart rates) is compared to a predetermined threshold activity level (or range of activity levels). The present inventors have recognized, among other things, that a patient activity level is a useful representation of a physiological state, such as for activating or adjusting rate smoothing.

In one example, a predetermined rate smoothing algorithm is mapped to at least one corresponding predetermined state. The rate smoothing algorithm is selected and applied while the corresponding predetermined state is present. In another example, one or more parameters of a rate smoothing algorithm are mapped to at least one corresponding predetermined state. These rate smoothing parameter(s) are selected and applied while the corresponding predetermined state is present. In one example, such rate smoothing parameters include an up-smoothing percentage to limit a speed of pacing rate increase and a down-smoothing percentage to limit a speed of pacing rate drop. In an alternative example, a rate smoothing algorithm is selected or adjusted based on a physiologic parameter monitored using a sensor. Other aspects of the invention will become apparent upon reading the following detailed description of the invention and viewing the accompanying drawings that form a part thereof.

BRIEF DESCRIPTION OF THE DRAWINGS

FIG. 13 illustrates an example of a method of selecting a rate smoothing algorithm based on a predetermined state.

FIG. 14 illustrates an example of a method of selecting parameters of a rate smoothing algorithm based on a predetermined state.

DETAILED DESCRIPTION

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

Rate smoothing provides a measure of control over the rate of change of the ventricular pacing rate. Specifically, the rate of change of the ventricular pacing rate is controlled on a cycle-to-cycle basis so as to maintain the rate of change within a programmed percentage of the previous cycle's rate. This function is achieved via the comparison of the ventricular pacing rate for each cycle to a "rate window" or percentage of the period for the previous cardiac cycle so as to ensure that the period of the pacing pulses is constrained from cycle to cycle by the limits defined by the rate window.

Controlling when and under what cardiac conditions to turn on/off or adjust the parameters for a rate smoothing program is highly advantageous. This control allows the rate smoothing to be deactivated when use of rate smoothing would be detrimental, or constraining, to a patient's need for rapid heart rate acceleration or deceleration. Furthermore, by selectively turning rate smoothing off or adjusting rate smoothing parameters, the number of pacing pulses delivered to a patient is reduced.

Figure 1:
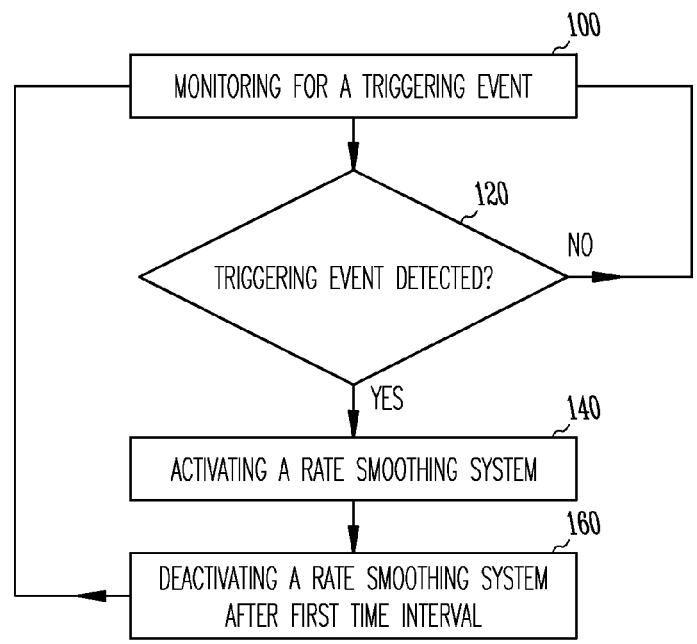
FIG. 1 shows one embodiment of a method according to the present invention.

FIG. 1 shows one embodiment of a method according to the present invention. At 100 a signal is sensed and analyzed for a triggering event. In one embodiment, the triggering event is any number of events sensed in either an activity signal coming from activity sensors (e.g., accelerometers, minute ventilation system, cardiac rate sensors) or a cardiac signal sensed from the patient's heart. In one embodiment, cardiac signals include either cardiac signals sensed from a ventricular location, or cardiac signals sensed from an atrial location.

At 120, the signal is then analyzed to detect the triggering event. When a triggering event is not detected, the signal continues to be analyzed. When a triggering event is detected, the rate smoothing system is activated at 140. Rate smoothing is then applied to control the changes in pacing rate as previously described. The rate smoothing is then deactivated at 160 at a time after activating the rate smoothing. In one embodiment, the time after activating the rate smoothing is a first time interval, where the first time interval is a programmable value. In an additional embodiment, the duration of the first time interval can also be changed based on information contained within either the activity or cardiac signals. Alternatively, the rate smoothing is deactivated based on information in the sensed activity signals or the cardiac signals, where the rate smoothing is deactivated when the one or more triggering events in the signals are no longer detected. Once the rate smoothing is deactivated, the system then returns to 100 to continue to monitor the signal for a triggering event.

Figure 2:
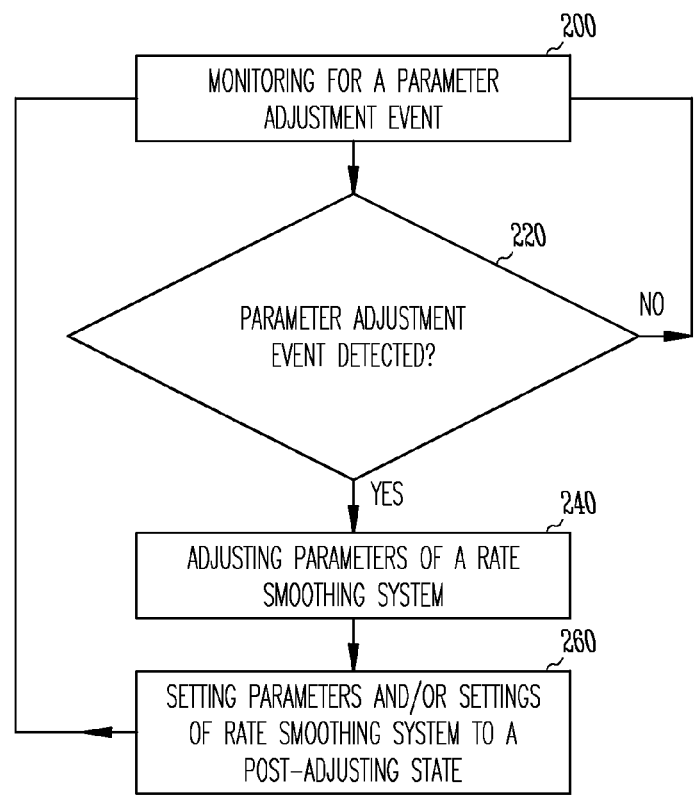
FIG. 2 shows one embodiment of a method according to the present invention.

FIG. 2 shows an additional embodiment of a method according to the present invention. At 200 a signal is sensed and analyzed for a parameter adjusting event. In one embodiment, the parameter adjusting event is any number of events sensed in the signal. For example, the signal can be an activity signal coming from activity sensors (e.g., accelerometers, minute ventilation system, cardiac rate sensors) or a cardiac signal sensed from the patient's heart. In one embodiment, cardiac signals include either cardiac signals sensed from a ventricular location, or cardiac signals sensed from an atrial location.

At 220, the signal is then analyzed to detect the parameter adjusting event. When a parameter adjusting event is not detected, the signal continues to be analyzed. When a parameter adjusting event is detected, parameters for the rate smoothing system are adjusted at 240. In one embodiment, adjusting the rate smoothing parameters includes making changes to parameter values for either up-smoothing or down-smoothing rate interval changes. For example, changes to the rate interval changes for down-smoothing can be made to set the rate interval in the range of six (6) to twelve (12) percent. Changes to the rate interval for up-smoothing can also be made to change the up-smoothing rate interval from, for example, 25 percent. Rate smoothing is then applied to control the changes in pacing rate as previously described. The parameters of the rate smoothing system are then set to a post-adjusting state at 260. In one embodiment, the post-adjusting state for the parameters and settings of the rate smoothing system includes restoring (i.e., resetting) the parameters and settings to their pre-parameter adjusting event state at a time after adjusting the parameters. Alternatively, adjusting the parameters of the rate smoothing system includes changing one or more of the original parameter values and/or settings (i.e., pre-trigger signal parameter state or pre-parameter adjusting event parameter state) to new parameters values and/or settings in a new parameter state. The new parameter state is then used in the rate smoothing system until a subsequent trigger signal and/or parameters adjusting event is detected. New parameter states can be created after each trigger signal and/or parameters adjusting event (e.g., a sequence of changes to the parameter values and/or settings for the rate smoothing system). This sequence of changes to the parameter values and/or settings also includes a change back to the original setting of the parameter values and/or settings of the rate smoothing system. In one embodiment, the changes to the parameter values and/or settings are based on information from sensed cardiac signals.

In one embodiment, the time after adjusting the parameters is a first time interval, where the first time interval is a programmable value. In an additional embodiment, the duration of the first time interval can also be changed based on information contained within either the activity or cardiac signals. Alternatively, the parameters of the rate smoothing are set to the post-adjusting state based on information in the sensed activity signals or the cardiac signals, where the rate smoothing parameters are set to the post-adjusting state when the one or more parameter adjusting events in the signals are no longer detected. Once the rate smoothing parameters are set to the post-adjusting state, the system then returns to 200 to continue to monitor the signal for a parameter adjusting event.

Figure 3:
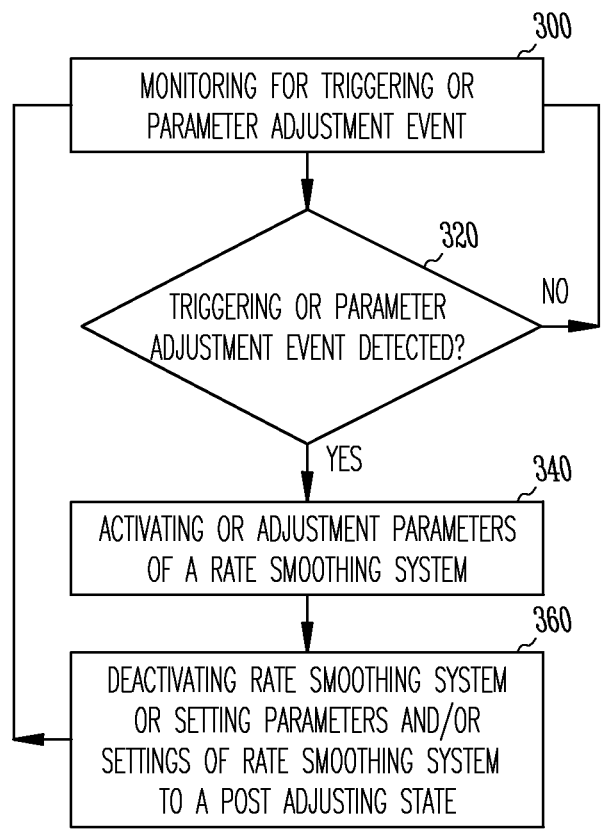
FIG. 3 shows one embodiment of a method according to the present invention.

FIG. 3 shows an addition embodiment of a method according to the present invention where a rate smoothing system can be controlled by both triggering events and parameter adjustment events. At 300 a signal is sensed and analyzed for a triggering event and/or parameter adjustment events, as previously described. At 320, the signal is then analyzed to detect either the triggering event or the parameter adjustment event. When a triggering event or a parameter adjustment event is not detected, the signal continues to be analyzed. When a triggering event or a parameter adjustment event is detected, however, the rate smoothing system is either activated (when a triggering event is detected) or parameters for the rate smoothing system are adjusted (when a parameter adjustment event is detected) at 340. With the present embodiment, it is possible that the rate smoothing is deactivated at 300, but is subsequently activated once a triggering event is detected. Once activated, sensed parameter adjustment events can cause the rate smoothing parameters to be adjusted.

At 360, either the rate smoothing is deactivated at a time after activating the rate smoothing, or the parameters of the rate smoothing system are set to the post-adjusting state at a time after adjusting the parameters, as previously described, where the time for either deactivating or setting the parameters and/or states of the rate smoothing system at the post-adjusting state are as previously described. Once the rate smoothing has either been deactivated or set to the post-adjusting state, the system then returns to 300 to continue to monitor the signal for the triggering event and/or the parameter adjusting event.

As previously discussed, there exists a variety of triggering and parameter adjusting events. In one embodiment, triggering events or parameter adjustment events are detected in one or more activity signals sensed by using activity monitors. Examples of activity monitors include accelerometers, minute ventilation systems or cardiac rate analyzer. In one embodiment, an activity signal is monitored from at least one of the activity monitors. The activity signal is analyzed to determine whether the activity signal has exceeded a first predetermined value. The triggering event and/or a parameter adjusting event are then detected when the activity signal exceeds the first predetermined value.

Examples of activity signals include a heart rate trajectory (heart rate vs. time) where the event is determined from the slope of the trajectory. Alternatively, the parameter adjusting event and/or the triggering event is detected when the cardiac rate exceeds a rate threshold. In an additional embodiment, the activity signal is an accelerometer signal from an accelerometer. In this embodiment, the amplitude (indication of motion) of the activity signal is analyzed to determine when the first predetermined value has been exceeded. In an alternative embodiment, the activity signal is a minute ventilation signal, where both the amplitude (depth of breath) and the frequency (breathing rate) of the signal are analyzed to determine if either has a value that exceeds the first predetermined value. In one embodiment, the first predetermined value is based on the type of activity sensor being utilized and the portion of the signal that is being analyzed. Programmed values for the first predetermined value will also depend upon the patient's cardiac condition and the type of implantable system that is used to treat the patient. Thus, values for the different applications of the first predetermined value need to be set on a patient-by-patient basis.

In an additional embodiment, triggering events or parameter adjustment events are found in monitored cardiac signals. For example, monitoring for the triggering event or parameter adjustment events includes monitoring a cardiac signal which includes indications of ventricular contractions or atrial contractions. When ventricular contractions are detected, the cardiac signal is analyzed for the occurrence of premature ventricular contractions (PVC). In one embodiment, PVCs are identified based on a comparison of contraction intervals, where PVCs have a shorter interval relative to preceding intervals. In addition, PVCs are also identified based on an analysis of the morphology of the complex wave form (e.g., the QRS-complex wave form), in addition to a contraction interval analysis. When one or more PVC occur, the triggering event or parameter adjustment event is detected.

Figure 4:
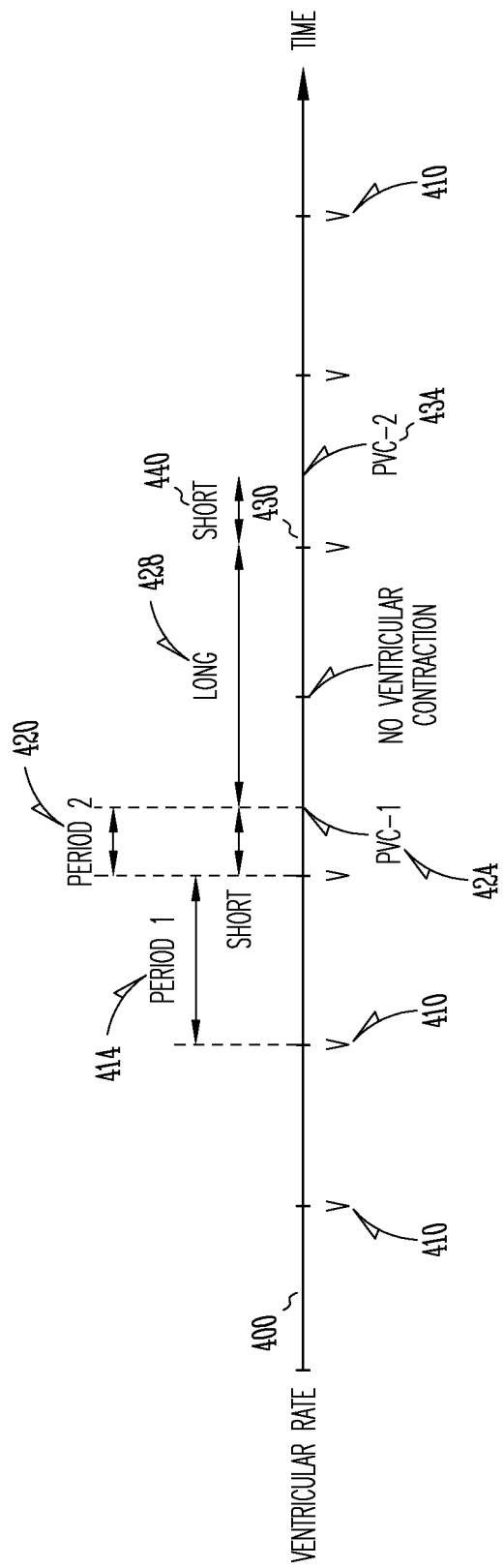
FIG. 4 is a timing diagram illustrating generally one example of a waveform illustrating a triggering and/or parameter adjusting event according to the present subject matter.

Alternatively, the cycle length pattern of cardiac cycles detected in the cardiac signal are used as triggering events or parameter adjustment events. For example, a detected short-long-short cycle length sequence from a cardiac signal is a triggering event or parameter adjustment event. FIG. 4 shows one embodiment of a cardiac signal with cardiac intervals having a short-long-short cycle length sequence. In one embodiment, the cardiac signal is a ventricular signal 400 having indications of ventricular contractions 410. The ventricular contractions 410 define cardiac intervals, where a first cardiac interval is shown at 414. A second cardiac interval 420 is shown occurring after the first cardiac interval 414. The second cardiac interval 420 is, however, shorter than the first cardiac interval 414. In one embodiment, the second cardiac interval 420 is shorter due to a PVC 424. If a rate smoothing function were operating as this ventricular signal is sensed, the change in the pacing rate would be based off of either the first cardiac interval 414 or the second cardiac interval 420.

After the second cardiac interval 420, there is a long interval 428. In one embodiment, the long interval 428 is not interrupted by a ventricular pacing pulse as the myocardium are not in the proper state to be captured by the pulse. Ventricular pace 430, however, captures the ventricles, where the ventricular pace 430 is followed by another PVC 434 which results in a second short interval 440. Once this pattern of short-long-short cardiac intervals is presented the triggering event or the parameter adjustment event is detected. The rate smoothing function is then either turned on, or the parameters of the operating rate smoothing system are adjusted.

In an alternative embodiment, triggering events or parameter adjustment events occur at selected times within a time interval. For example, monitoring for the triggering event or parameter adjustment events includes monitoring a time interval, such as the time of the day, week, month, year, or an event, such as a season of the year. The triggering event or parameter adjustment event is then detected at a first time in the time interval, where the first time is either programmed by the physician or set based on the implantable systems analysis of one or more detected signals. For example, when it is known by the physician or determined by the implantable pulse generator that a patient does not experience tachyarrhythmia during a certain time of the day (e.g., in the hours between 12 midnight and 4 a.m.) the triggering event (to turn the rate smoothing off) or the parameter adjustment event can be programmed as occurring at 12 midnight, with the duration of the first time interval lasting for approximately 4 hours.

In an additional embodiment, the triggering event or parameter adjustment event is when a pacemaker mode is changed. For example, when the pacemaker is switched from one mode of operation (e.g., DDD) to a second mode of operation (DVI) a triggering event or parameter adjustment event is detected. Alternatively, the triggering event or parameter adjustment event is when one or more pacing parameters are changed.

Other triggering events or parameter adjustment events include analyzing one or more cardiac signals to detect the occurrence of an arrhythmic episode. In one embodiment, the arrhythmic episodes can include ventricular tachycardias or ventricular bradycardias. Once the arrhythmic episode is treated, an end to the arrhythmic episode is identified. Once the end of the arrhythmic event is identified, the triggering event or parameter adjusting event is declared. The stability of the intervals can also be used as either a triggering event or a parameter adjusting event. In one embodiment, a stability analysis measures the consistency, or variability, of intervals for the sensed contractions. For example, as a cardiac signal is sensed, the consistency of the sensed cardiac intervals are analyzed. When the variability in the cycle length intervals exceeds a set value a stability problem is declared. Once declared, the triggering event or the parameter adjusting event is identified. The user can also request that a triggering event or a parameter adjusting event be considered. In this embodiment, the system receives a request for either a triggering event (e.g., to turn on rate smoothing) or a parameter adjustment event (e.g., make changes to the parameters). The system analyzes the cardiac condition and either issues or denies the request to issue the parameter adjusting event or the triggering event based on the analysis of the cardiac condition.

Figure 5:
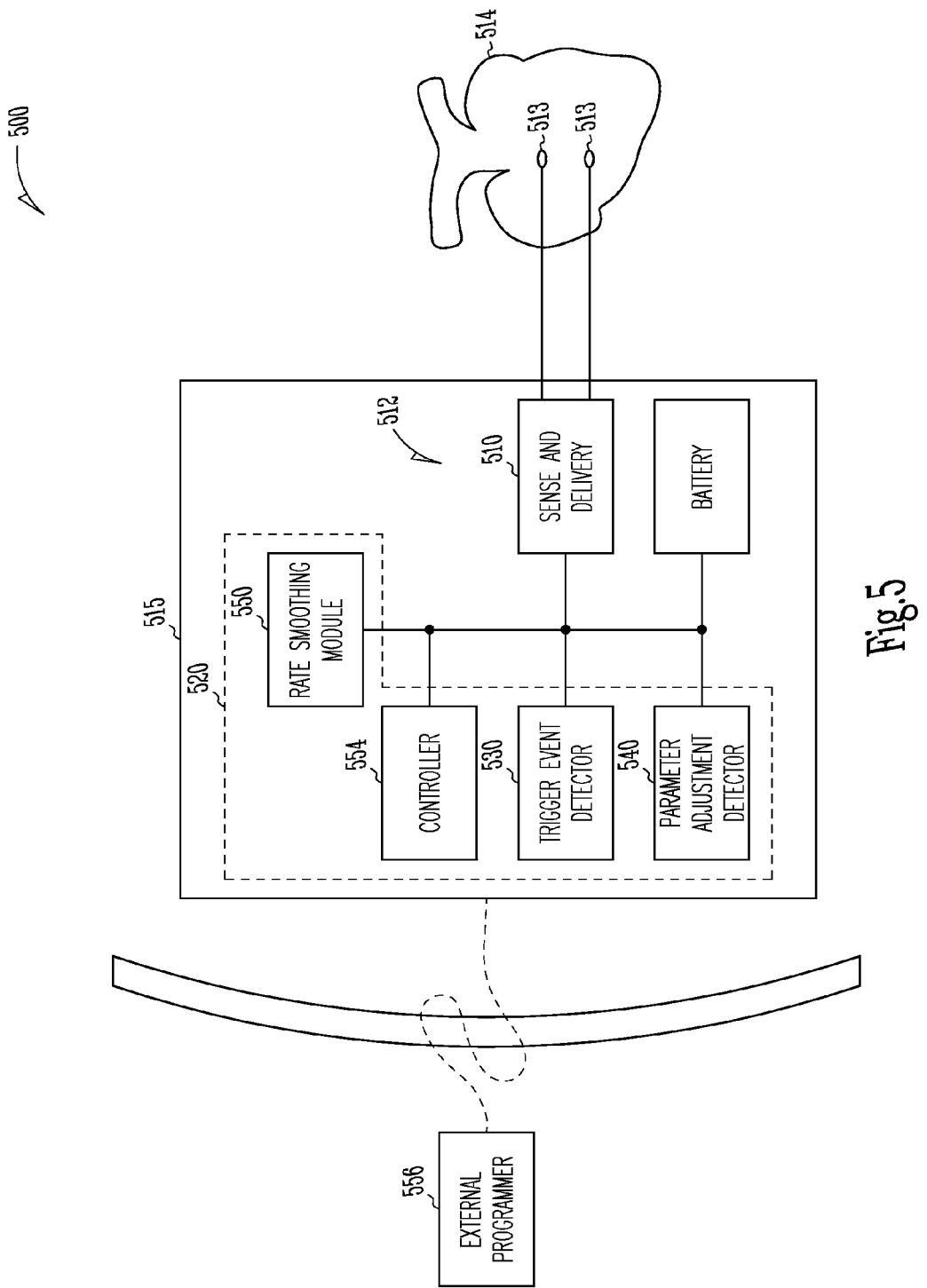
FIG. 5 is a block diagram of one embodiment of an implantable medical device according to the present subject matter.

FIG. 5 shows one embodiment of a system 500 according to the present subject matter. The system includes a signal input system 510, where the signal input system 510 is adapted to monitor a signal. In one embodiment, the signal is any of the signals previously discussed. In the embodiment shown in FIG. 5, the signal input system 510 is a cardiac signal sensing system 512, which includes cardiac electrodes 513 implanted in or on the heart 514 to allow for cardiac signals to be sensed. In one embodiment, the cardiac electrodes 513 are coupled to an implantable pulse generator housing 515, and the control circuitry 520 therein, to allow for either unipolar or bipolar cardiac signals to be sensed from the supraventricular region and/or the ventricular region of the heart 514. Pacing pulses can also be delivered to either the supraventricular and/or ventricular region of the heart through the cardiac electrodes 513 under the control of the cardiac signal sensing system 512 and the control circuitry 520.

The system 500 includes control circuitry 520, where the control circuitry 520 is coupled to the signal input system 510. The control circuitry 520 receives the signal from the signal input system 510, where the signal is processed by the control circuitry 520. The control circuitry 520 includes a trigger event detector 530, where the trigger event detector 530 analyzes the signal to detect a trigger event. The control circuitry 520 further includes a parameter adjustment event detector 540, where the parameter adjustment event detector 540 analyzes the signal to detect a parameter adjustment event. The control circuitry 520 further includes a rate smoothing module 550, where the rate smoothing module 550 executes the rate smoothing protocols and makes changes to the rate smoothing parameters once parameter adjustment events are identified. In one embodiment, the components of the control circuitry 520 are under the control of a microcontroller 554. The control circuitry 520 also has communication circuitry which allows the implantable system 500 to communicate with an external programmer 556.

In one embodiment, the cardiac signal sensing system 512 senses and analyzes a ventricular cardiac signal. The ventricular cardiac signal is then analyzed by the trigger event detector 530 and the parameter adjustment event detector 540 to detect any occurrence of a series of consecutive ventricular intervals having a short-long-short sequence as previously discussed. In addition, the trigger event detector 530 and the parameter adjustment event detector 540 also analyze the ventricular cardiac signal to detect premature ventricular contractions in the ventricular cardiac signal as previously discussed.

Figure 6:
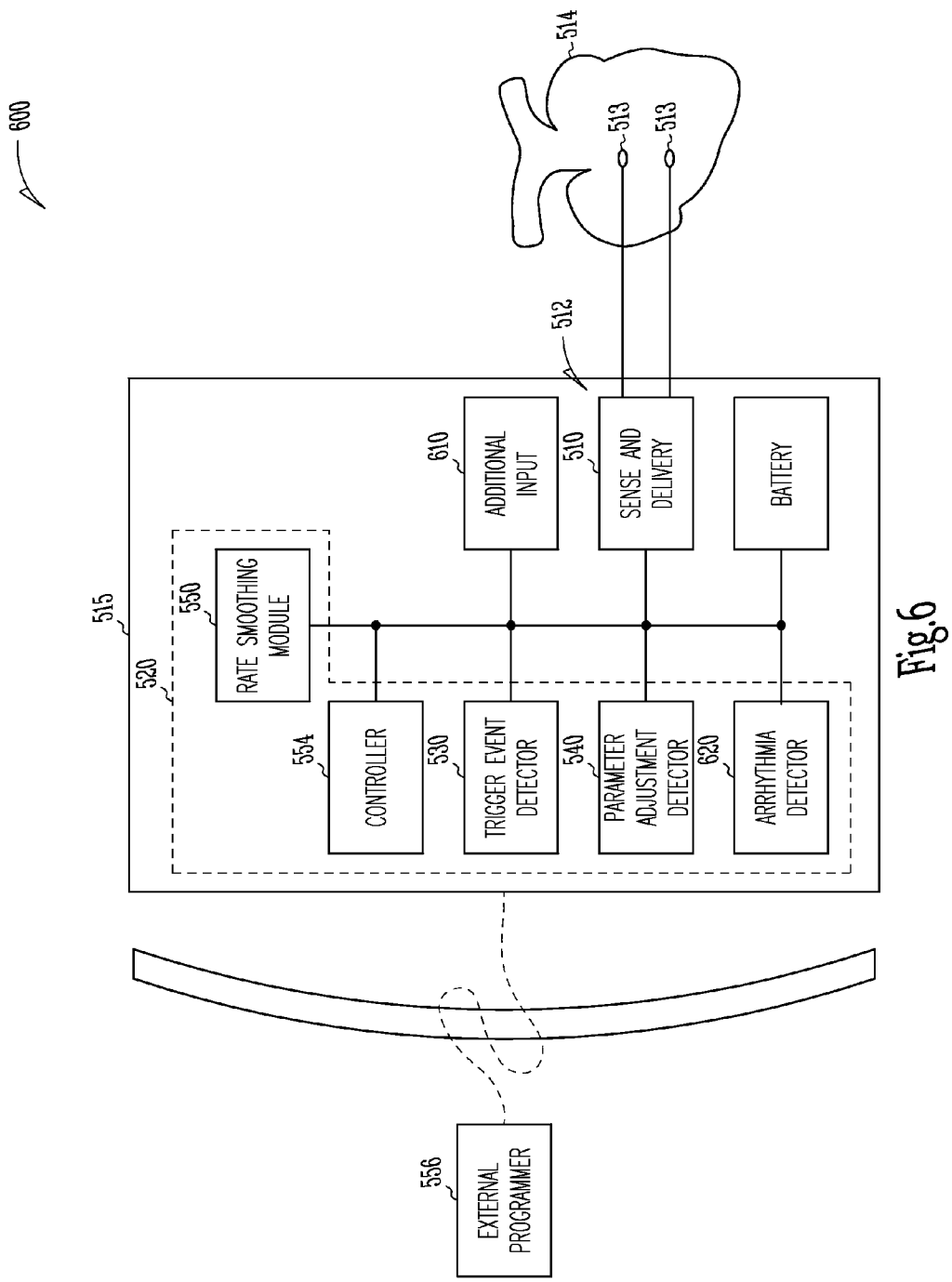
FIG. 6 is a block diagram of one embodiment of an implantable medical device according to the present subject matter.

FIG. 6 shows an additional embodiment of a system 600 according to the present subject matter. The system 600 includes components similar to those in system 500, but system 600 further includes at least one additional input 610 into the signal input system. In one embodiment, the additional input 610 is a minute ventilation sensor. Signals from the minute ventilation sensor are delivered to both the trigger event detector 530 and the parameter adjustment detector 540. The trigger event detector 530 and the parameter adjustment detector 540 then analyze the signals from the minute ventilation sensor to determine when the signal exceeds a first value, as previously discussed.

In an alternative embodiment, the additional input 610 is an accelerometer sensor. Signals from the accelerometer sensor are delivered to both the trigger event detector 530 and the parameter adjustment detector 540. The trigger event detector 530 and the parameter adjustment detector 540 then analyze the signals from the accelerometer sensor to determine when the signal exceeds a first value, as previously discussed.

FIG. 6 also shows the control circuitry 520 further including an arrhythmia detection circuit 620. In one embodiment, the arrhythmia detection circuit 620 is coupled to the signal input system 510 and receives and analyzes ventricular cardiac signal to detect an arrhythmic episode, including an end to the arrhythmic episode. The trigger event detector 530 and the parameter adjustment detector 540 then declare events at the end of the arrhythmic episode.

Figure 7:
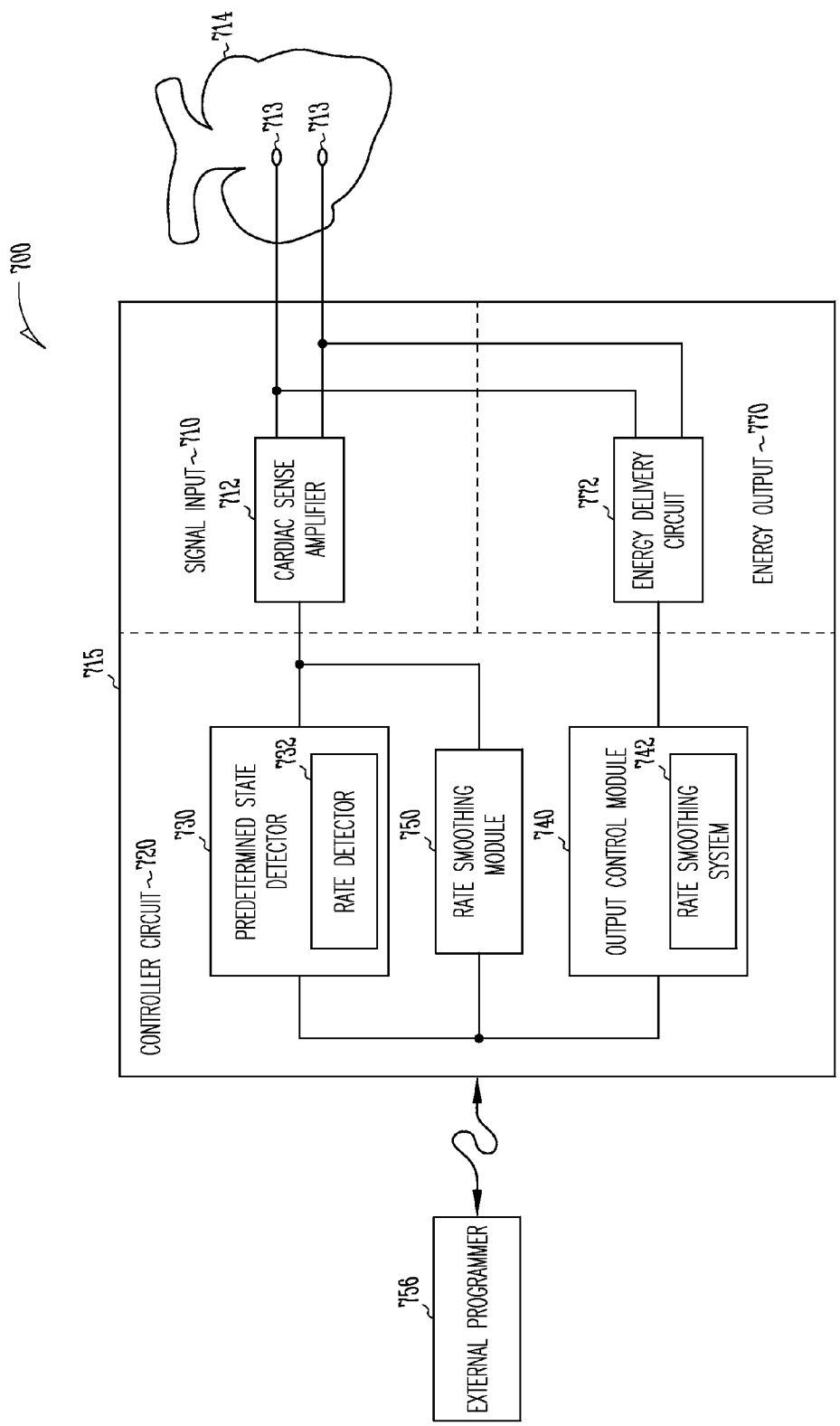
FIG. 7 is a block diagram showing an example of an implantable system providing or adjusting rate smoothing based on whether a predetermined state is present.

FIG. 7 is a block diagram that shows an example of portions of an implantable system 700 providing and/or adjusting rate smoothing based on whether a predetermined state is present. System 700 includes a signal input circuit 710 adapted to monitor at least one signal. In the example of FIG. 7, the signal is a cardiac signal representing heart contractions, from which a heart rate may be measured. Signal input 710 includes at least one cardiac sense amplifier 712. One or more cardiac electrodes 713, coupled to amplifier 712 and associated with a heart 714, allow for unipolar or bipolar cardiac signals to be sensed from a supraventricular region and/or a ventricular region of heart 714. The supraventricular region may include an atrial region.

System 700 further includes an energy output circuit 770, coupled to electrodes 713, to deliver electrical energy pulses to the supraventricular or ventricular regions of heart 714. This delivery of energy pulses to "capture" the heart by triggering resulting heart contractions is referred to as pacing. In one example, cardiac electrodes 713 are coupled to implantable pulse generator housing 715, energy delivery circuit 772, and/or amplifier 712 to allow for unipolar or bipolar pacing of the supraventricular region and/or a ventricular region of heart 714 using electrodes 713. Housing 715 may also function as a reference electrode for unipolar sensing and/or pacing.

System 700 further includes a controller circuit 720, coupled to signal input 710 and energy output 770. Controller 720 receives and analyzes the cardiac signal from amplifier 712. Controller 720 includes an output control module 740, a rate smoothing module 750, and a predetermined state detector 730. Output control module 740 receives inputs from signal input 710 and rate smoothing module 750, determines a pacing rate, and controls energy output 770 to deliver energy pulses to heart 714 at the pacing rate. The pacing rate may be calculated, on a beat-by-beat basis, using a predetermined pacing algorithm. The pacing algorithm defines the timing of the delivery of energy pulses to heart 714 based on the sensed cardiac signal and predetermined parameters such as maximum and minimum pacing rates.

Rate smoothing module 750 may be implemented in hardware, software, and/or firmware to execute at least one rate smoothing algorithm. The rate smoothing algorithm limits a pacing rate based on a preceding heart rate. Output control module 740 includes a rate smoothing system 742 coupled to rate smoothing module 750. In one example, rate smoothing module 750 provides rate smoothing system 742 with rate smoothing parameters including an up-smoothing percentage to limit a speed of pacing rate increase and a down-smoothing percentage to limit a speed of pacing rate drop. The up-smoothing percentage and the down-smoothing percentage may have different or identical values. It may be desirable to use an up-smoothing percentage that is different from a down-smoothing percentage during a particular range of heart rates. For example, when the heart rate is very high, it may be desirable to prevent further increase of heart rate by using a zero up-smoothing percentage while allowing a quick drop of heart rate by using a relatively large down-smoothing percentage. In one example, rate smoothing system 742 multiplies a present heart rate by the up-smoothing percentage.

The result is added to the present heart rate to obtain an up-smoothing limit. Rate smoothing system 742 also multiplies the present heart rate by the down-smoothing percentage. The result is subtracted from the present heart rate to obtain a down-smoothing limit. The up-smoothing and down-smoothing limits, updated on a beat-by-beat basis in one example, form a window within which the pacing rate may vary for the next heart beat. If the pacing rate calculated by output control module 740 exceeds the up-smoothing limit or drops below the down-smoothing limit, the pacing rate is instead set to the corresponding one of the up-smoothing limit or the down-smoothing limit.

State detector 730 determines whether a state of the sensed signal matches one or more predetermined states. In the example of FIG. 7, state detector 730 includes a rate detector 732 to detect a patient's supraventricular or ventricular heart rate and to determine whether the heart rate exceeds a predetermined threshold representative of a predetermined state, or alternatively, whether the heart rate is below the predetermined threshold representative of a different predetermined state, or still alternatively, whether the heart rate is within a predetermined range representative of a still different predetermined state. In one example, rate detector 732 includes a comparator having a heart rate input and a predetermined threshold input, and a comparator output representative of whether the heart rate represents the predetermined state. The predetermined threshold input is coupled to a storage medium including one or more threshold value(s) representative of the predetermined state(s). Examples of the predetermined states include: (1) a high rate; (2) a low rate; and (3) a intermediate rate. Alternatively, the predetermined state(s) may include one or more predetermined range(s).

In addition to executing a rate smoothing algorithm, rate smoothing module 750 may select and/or adjust a rate smoothing algorithm. In one operative example, rate smoothing module 750 selects a particular rate smoothing algorithm from the storage medium upon detecting a change in the signal state. In another operative example, rate smoothing module 750 adjusts at least one parameter of a rate smoothing algorithm upon detecting a change in the signal state. Examples of parameters of a rate smoothing system include up-smoothing and down-smoothing percentages, as previously described.

In one example, controller circuit 720 also includes communication circuitry that allows implantable system 700 to communicate with an external programmer 756, which provides a user-interface for implantable system 700. In one example, a physician uses programmer 756 to evaluate the cardiac condition of a patient, program implantable system 700 such as to deliver at least one type of therapy, extract a cardiac condition history and/or therapy history stored in implantable system 700, or obtain information about the operative status of implantable system 700.

Figure 8:
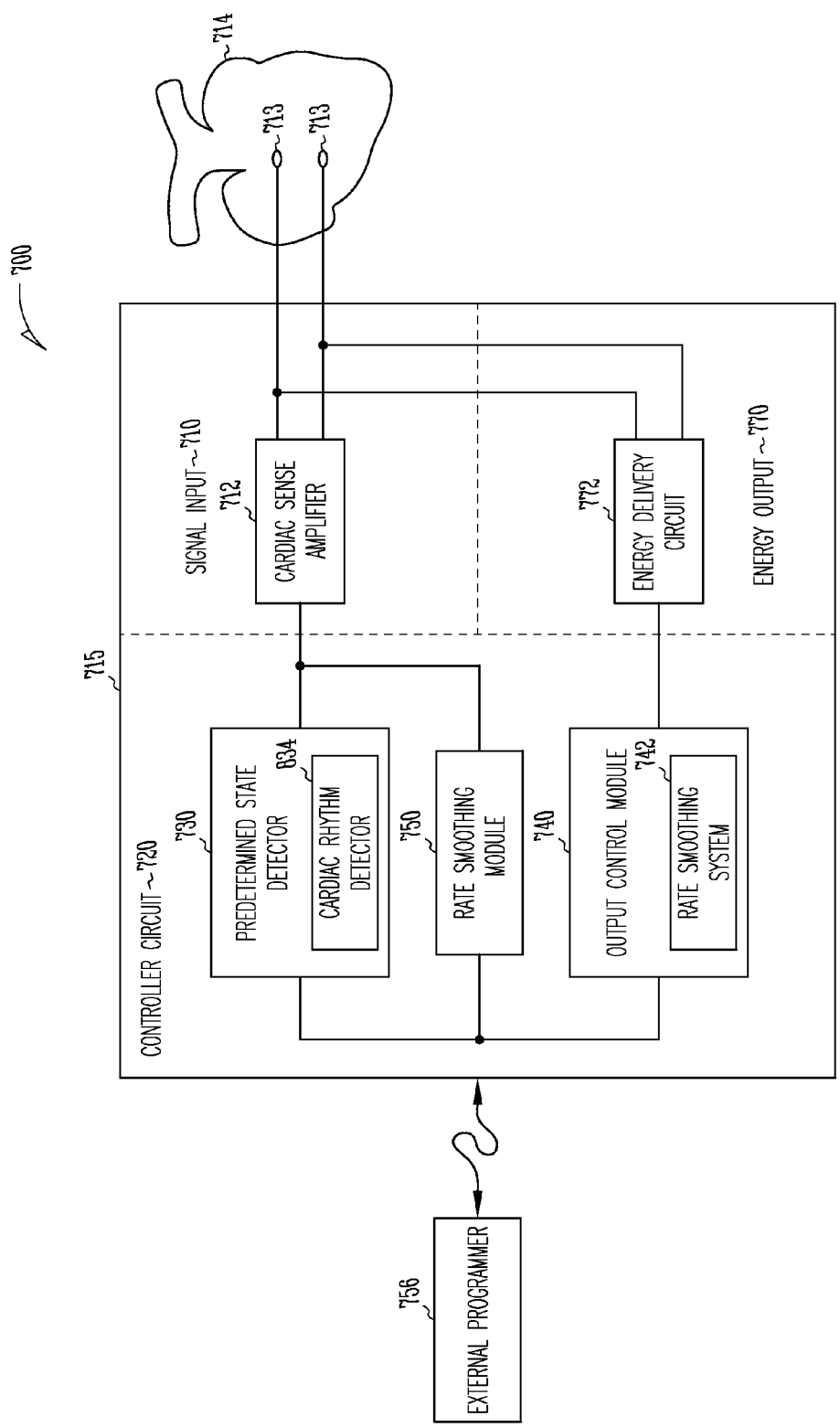
FIG. 8 is a block diagram showing another example of an implantable system providing or adjusting rate smoothing based on whether a predetermined state is present.

FIG. 8 is a block diagram that shows another example of an implantable system 700 providing or adjusting rate smoothing based on whether a predetermined state is present. In this example, state detector 730 includes a cardiac rhythm detector 834 to analyze a cardiac signal representing a patient's heart contractions in a temporal pattern referred to as a cardiac rhythm, and to determine whether the cardiac rhythm matches one or more predetermined cardiac rhythms, such as a normal sinus rhythm, an atrial tachycardia, an atrial fibrillation, a ventricular tachycardia, a ventricular fibrillation, or a bradycardia. One example of a suitable rhythm determination system is discussed in Hsu et al. U.S. Pat. No. 6,266,554 ("the Hsu et al. patent"), entitled "System and Method for Classifying Cardiac Complexes," which is assigned to Cardiac Pacemakers, Inc., and incorporated by reference herein in its entirety.

In the example of FIG. 8, it may be desirable to apply different rate smoothing algorithms or alternatively, to apply different parameters for a rate smoothing algorithm, for different cardiac rhythm states. In one example, a particular rate smoothing algorithm, or particular parameters of a rate smoothing algorithm, may be used to prevent an arrhythmia or to facilitate recovery from an arrhythmia. For example, during an atrial fibrillation cardiac rhythm state, it may be desirable to prevent further increase of atrial heart rate by using a zero up-smoothing percentage while allowing a quick drop of heart rate by using a very large down-smoothing percentage.

Figure 9:
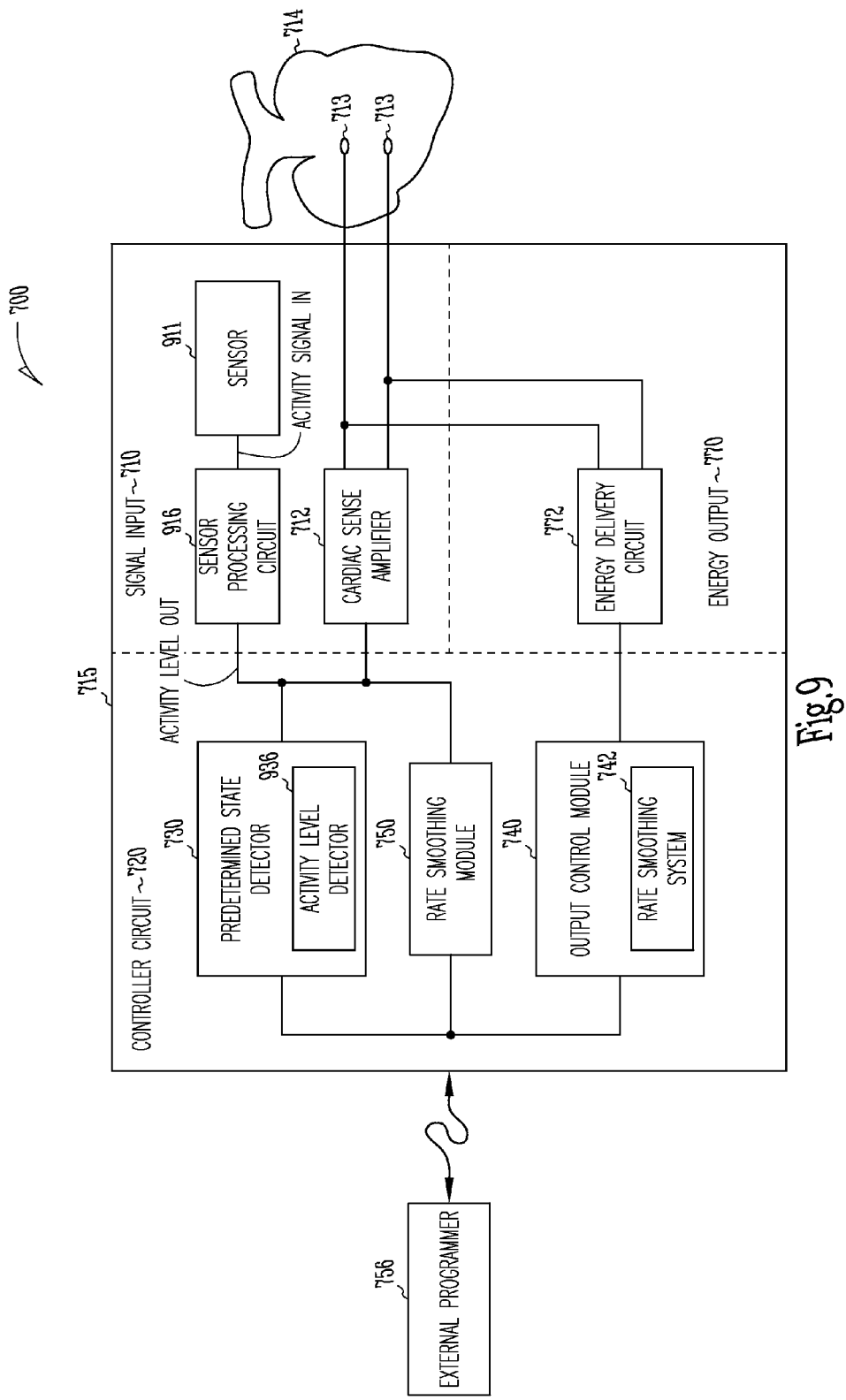
FIG. 9 is a block diagram showing yet another example of an implantable system providing or adjusting rate smoothing based on whether a predetermined state is present.

FIG. 9 is a block diagram that shows yet another example of an implantable system 700 providing or adjusting rate smoothing based on whether a predetermined state is present. In this example, signal input 710 further includes a sensor processing circuit 916. A sensor 911, coupled to processing circuit 916, allows for monitoring a patient's physical activity which represents the patient's metabolic need for a particular approximate heart rate. Examples of sensor 911 include a respiration sensor and/or accelerometer or any other suitable sensor for indicating the patient's metabolic need. The choice of a particular sensor is typically based on its efficacy in indicating a patient's metabolic need. Processing circuit 916 processes a signal output by sensor 911 so that the activity level is readable by state detector 730 and output control module 740. In one example, processing circuit 916 translates an activity signal, at a frequency of the patient's activity, to a more slowly varying signal representing an activity level. In this example, output control module 740 is coupled to both cardiac sense amplifier 712 and processing circuit 916. Output control module 740 calculates the pacing rate based on the activity level and the sensed cardiac signal.

In the example of FIG. 9, state detector 730 includes an activity level detector 936. Activity level detector 936 determines whether the activity level output from processing circuit 916 exceeds a predetermined activity level, or alternatively, whether it is below a predetermined activity level, or still alternatively, whether it falls within a predetermined range of activity levels. In one example, activity level detector 936 includes a comparator having an activity level input and a predetermined activity level input, and a comparator output representative of whether the activity level matches the predetermined state.

It may be desirable to apply different rate smoothing algorithms or alternatively, to apply different parameters for a rate smoothing algorithm, based on a patient's metabolic need for a particular range of heart rates. In one example, the algorithm or parameter selection is used to allow heart rate to increase quickly to meet the metabolic need resulting from exercise. In one example, a first rate smoothing algorithm having a single rate-smoothing percentage parameter is selected when the activity level is below a predetermined activity level (e.g., during a rest). The single rate-smoothing percentage parameter typically has a moderate value and is used for calculating both up-smoothing and down-smoothing limits. When the activity level exceeds the predetermined activity level (e.g., during an exercise), a second rate smoothing algorithm is selected. The second rate smoothing algorithm includes at least a up-smoothing percentage and a different down-smoothing percentage, allowing a quick increase of heart rate by using a relatively large up-smoothing percentage, while inhibiting a quick drop of heart rate by using a zero or a relatively small down-smoothing percentage. In an alternative example, one rate-smoothing algorithm including at least independent up-smoothing and down-smoothing percentage parameters is used at different activity levels. When the activity level is below a predetermined activity level, the up-smoothing and down-smoothing percentages are set to the same value. When the activity level exceeds the predetermined activity level (e.g., during an exercise), the up-smoothing percentage is set to a relatively large value to allow a quick increase of heart rate, while the down-smoothing percentage is set to zero or a relatively small value to inhibit a quick drop of heart rate.

Figure 10:
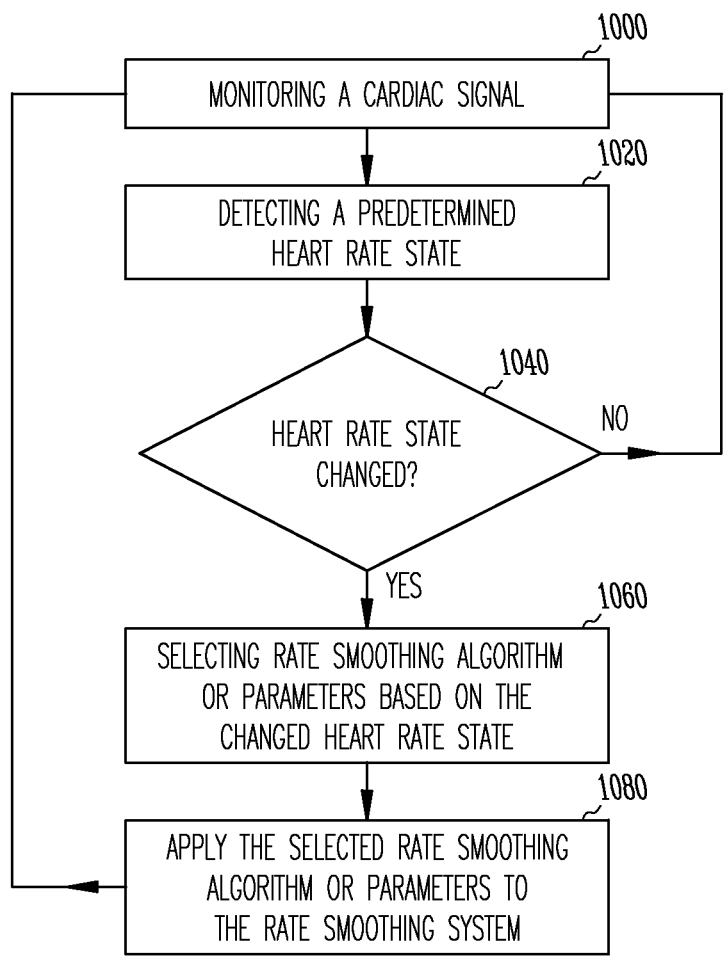
FIG. 10 is a flow chart showing an example of a method of adjusting rate smoothing based on whether a predetermined state is present.

FIG. 10 is a flow chart that shows an example of a method of adjusting rate smoothing based on whether a predetermined state is present. At 1000 a cardiac signal is monitored. The cardiac signal is sensed from an electrode associated with a patient's heart and represents the patient's heart contractions from which a heart rate can be measured. In one example, the cardiac signal is sensed from at least one atrial location. In another example, the cardiac signal is sensed from at least one ventricular location. At 1020, the cardiac signal is analyzed to determine whether it matches a predetermined heart rate state. This includes determining whether the heart rate exceeds a predetermined threshold value or, alternatively, whether the heart rate falls within a predetermined heart rate range. At 1040, if the heart rate changes state, a particular rate smoothing algorithm, or alternatively, one or more particular parameters of the rate smoothing algorithm, are selected or adjusted, at 1060, based on the changed heart rate state. At 1080, the selected rate smoothing algorithm, or the one or more parameters of the rate smoothing algorithm, are applied to the rate smoothing system.

Figure 11:
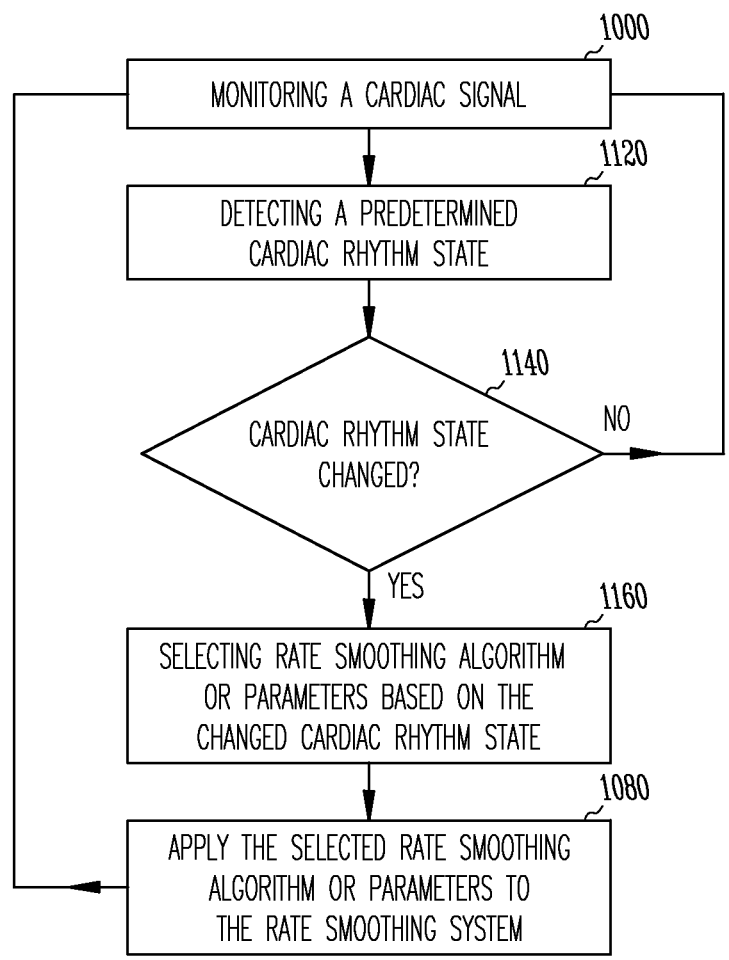
FIG. 11 is a flow chart showing an example of another method of adjusting rate smoothing based on whether a predetermined state is present.

FIG. 11 is a flow chart that shows an example of another method of adjusting rate smoothing based on whether a predetermined state is present. In this example, in which the cardiac signal at 1000 represents a patient's heart contractions in a temporal pattern referred to as a cardiac rhythm 1120, includes determining whether the cardiac signal manifests one of several possible predetermined cardiac rhythms. Such predetermined cardiac rhythms include a normal sinus rhythm, an atrial tachycardia, an atrial fibrillation, a ventricular tachycardia, a ventricular fibrillation, and a bradycardia. One example of a suitable rhythm determination method is discussed in the Hsu et al. patent, which was above incorporated by reference in its entirety. If the cardiac rhythm state changes at 1140, a rate smoothing algorithm, or alternatively, one or more parameters of the rate smoothing algorithm, are selected at 1160 based on the changed cardiac rhythm state.

Figure 12:
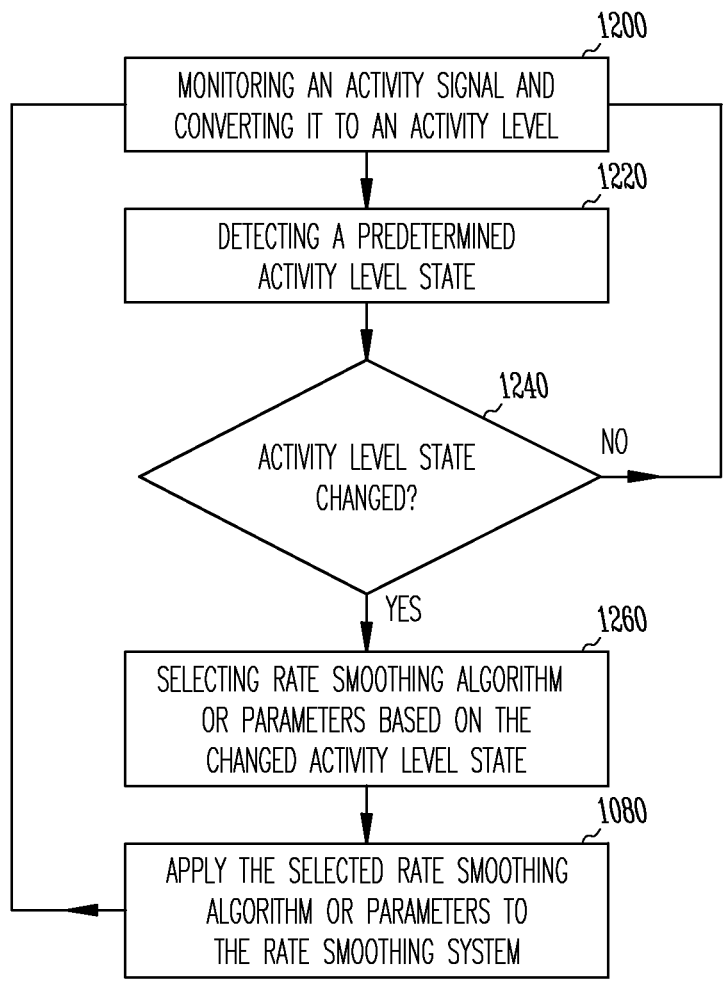
FIG. 12 is a flow chart showing an example of yet another method of adjusting rate smoothing based on whether a predetermined state is present.

FIG. 12 is a flow chart that shows an example of yet another method of adjusting rate smoothing based on whether a predetermined state is present. At 1200 an activity signal is monitored and translated to an activity level. The activity signal is sensed from an accelerometer or a respiration sensor and represents a patient's metabolic need for a particular heart rate range. The activity signal, representing a frequency of a patient's activity, is dynamically translated to a more slowly varying signal representative of the activity level. At 1220, the activity level is analyzed to determine whether it matches a predetermined activity level state. This includes determining whether an activity level exceeds a predetermined threshold activity level or, alternatively, falls within a predetermined range of activity levels. If the activity level state changes at 1240, a rate smoothing algorithm, or alternatively, one or more parameters of the rate smoothing algorithm, is selected at 1260 based on the changed activity level state.

FIG. 13 illustrates an example of a method for selecting a rate smoothing algorithm based on a predetermined state. The selection includes mapping a predetermined rate smoothing algorithm to a predetermined state using a look-up table. The look-up table includes predetermined states 1300 and predetermined rate smoothing algorithms 1320, labeled by numbers and letters, respectively, in the example of FIG. 13. Predetermined states may include one or more of heart rate states, cardiac rhythm states, and activity level states, as previously discussed. For example, while predetermined state #1 is present, rate algorithm A will be selected and applied to the rate smoothing system.

FIG. 14 illustrates an example of a method of selecting parameters of a rate smoothing algorithm based on a predetermined state. In this example, the parameters of the rate smoothing algorithm include an up-smoothing percentage 1450 and a down-smoothing percentage 1460. The parameter selection includes mapping rate smoothing percentages 1450 and 1460 to predetermined state 1300 using a look-up table. For example, while predetermined state #3 is present, 15% and 10% will be selected for the up-smoothing percentage and the down-smoothing percentage, respectively, and applied to the rate smoothing system.

Figure 15:
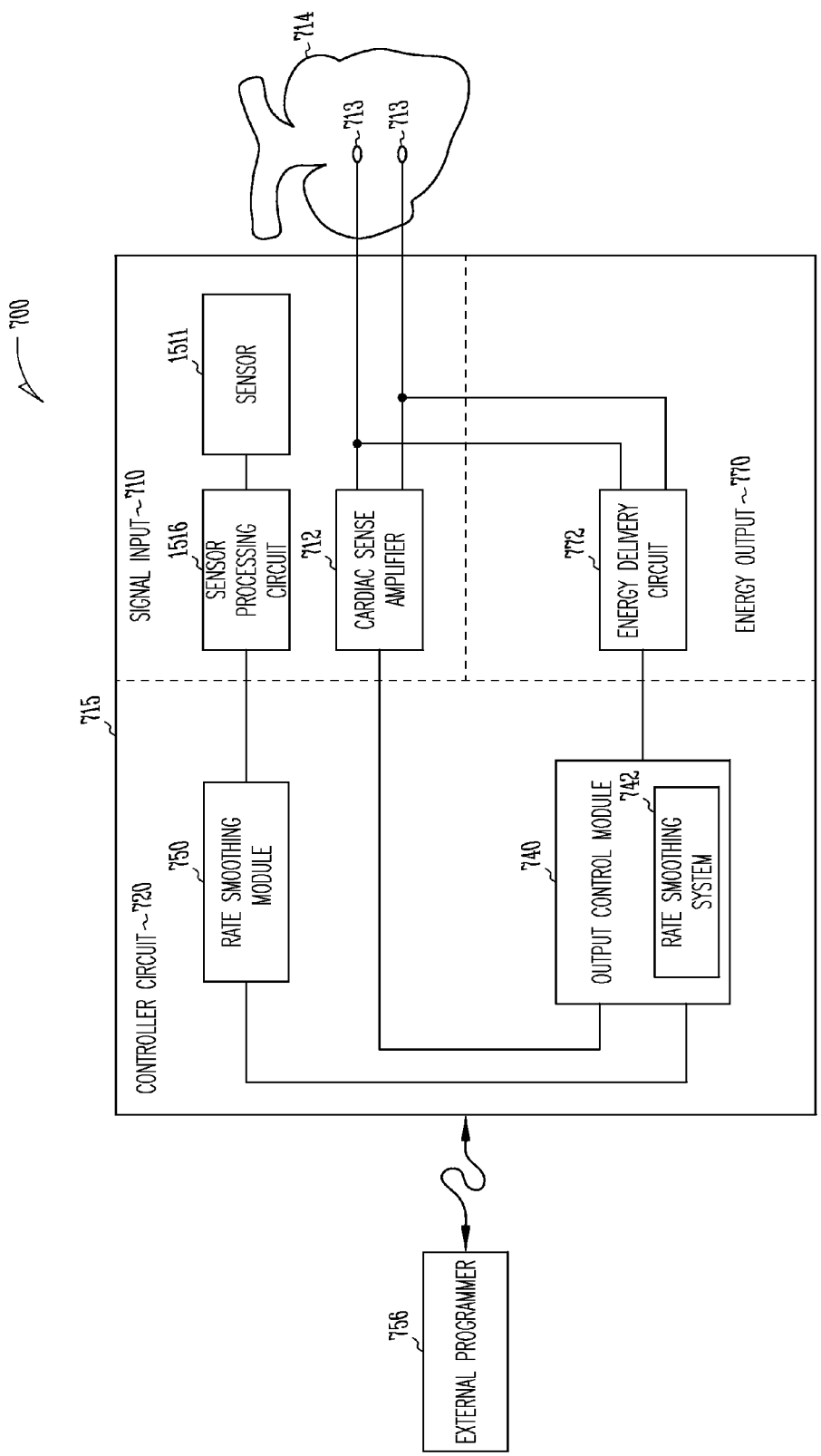
FIG. 15 is a block diagram showing one example of an implantable system providing or adjusting rate smoothing based on a physiologic parameter monitored using a sensor.

In general, the techniques discussed in this document permit rate smoothing to be activated and/or deactivated, or one or more rate smoothing parameters to be adjusted based on any sensed physiological parameter other than intrinsic electrical cardiac depolarizations, as illustrated generally by FIG. 15. FIG. 15 is a block diagram of one example of an implantable system 700 providing (e.g., activating and/or deactivating) or adjusting rate smoothing based on a sensed physiologic. In this example, signal input 710 includes a sensor 1511 coupled to rate smoothing module 750 by a sensor processing circuit 1516 that provides any needed signal preprocessing. Sensor 1511 monitors a physiologic parameter other than intrinsic electrical cardiac depolarizations. The monitored physiological parameter may relate to heart condition or function. Examples of sensor 1511 include a metabolic need sensor, such as a respiration sensor or accelerometer, that provide, among other things, an indication of a metabolic need for a particular heart rate. Other examples of sensor 1511 include a heart function sensor, such as an intracavitary or other pressure sensor or a cardiac contractility sensor. In one example, rate smoothing module 750 provides rate smoothing system 742 with rate smoothing activated and/or deactivated based on the physiologic parameter sensed by sensor 1511. In another example, rate smoothing module 750 calculates one or more rate smoothing parameters based on the physiologic parameter sensed using sensor 1511. Examples of such rate smoothing parameters include an up-smoothing percentage to limit a speed of pacing rate increase and a down-smoothing percentage to limit a speed of pacing rate drop. In the example of FIG. 15, the smoothed pacing rate is calculated based on the physiological parameter, the sensed cardiac signal, and a preceding cardiac interval.

Thus, in FIG. 15, system 700 is capable of providing, among other things, cardiac pacing and/or cardiac resynchronization therapy at a physiological sensor-indicated rate and, furthermore, the physiological sensor-indicated rate is smoothed by a rate smoothing function that uses a physiologic parameter to activate and/or deactivate the rate smoothing and/or to adjust a rate smoothing parameter (e.g., up-smoothing and/or down-smoothing). One example, in which activating, deactivating, and/or adjusting rate smoothing using a physiologic parameter may be desirable is in a heart that has undergone a myocardial infarction. In some post-infarct patients, it may be important to regulate left ventricular heart wall stress to prevent congestive heart failure (CHF) that may result from remodeling of neurological heart signal conduction paths after the myocardial infarction. One technique of regulating heart wall stress is to elevate ventricular heart rate (by increasing a ventricular pacing rate) to reduce stroke volume and pulse pressure and, in turn, to reduce heart wall stress. In this application, the rate of change of heart wall stress may also be an important consideration. For example, it may be desirable to gradually increase or decrease the load placed on the left ventricle during rate-adaptive pacing (analogous to a skeletal muscle injury in which a skeletal muscle is gradually worked back to normal function). For this application, system 700 of FIG. 15 could provide rate smoothing that provides a variable degree of control over pacing rate increases and decreases, based on pressure and/or contractility measurements. Similarly, the activation, deactivation, and/or parameter adjustment of rate smoothing discussed in this document could be based on any other physiologic sensor, and is not limited to the particular physiologic sensors delineated herein.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A cardiac pacing system, comprising:
   a sensor configured to monitor a physiologic parameter other than intrinsic electrical cardiac depolarizations, the physiologic parameter including a physical activity;
   a processing circuit coupled to the sensor, the processing circuit configured to translate the physical activity into an activity level;
   a state detector coupled to the processing circuit, the state detector configured to detect a predetermined state of the physiologic parameter and including an activity level detector configured to determine whether the activity level matches the predetermined state of the physiologic parameter by comparing the activity level to one or more predetermined activity levels; and
   a controller circuit configured to determine and control a pacing rate, the controller circuit including a rate smoothing module configured to perform rate smoothing that limits a rate of change in the pacing rate, the rate smoothing module coupled to the state detector and configured to receive the physiologic parameter and activate the rate smoothing, deactivate the rate smoothing, or adjust one or more rate smoothing parameters of the rate smoothing in response to a detection of the predetermined state of the physiologic parameter.

2. The system of claim 1, wherein the sensor is configured to provide an indication of a metabolic need for a heart rate.

3. The system of claim 2, wherein the sensor comprises an accelerometer.

4. The system of claim 2, wherein the sensor comprises a respiration sensor.

5. The system of claim 1, wherein the sensor is configured to monitor a cardiac function.

6. The system of claim 5, wherein the sensor comprises a pressure sensor.

7. The system of claim 5, wherein the sensor comprises a cardiac contractility sensor.

8. The system of claim 1, wherein the rate smoothing module is configured to limit a speed of pacing rate increase using a first rate smoothing percentage.

9. The system of claim 8, wherein the rate smoothing module is configured to limit a speed of pacing rate drop using a second rate smoothing percentage.

10. The system of claim 9, wherein the controller circuit further comprises a parameter adjusting event detector configured to detect a parameter adjusting event from the physiologic parameter, and the rate smoothing module is configured to adjust the first rate smoothing percentage and the second rate smoothing percentage in response to a detection of the parameter adjusting event.

11. The system of claim 10, wherein the rate smoothing module is configured to calculate the first rate smoothing percentage and the second rate smoothing percentage using the physiologic parameter.

12. The system of claim 11, wherein the controller circuit further comprises a trigger event detector configured to detect a trigger event from the physiologic parameter, and the rate smoothing module is configured to activate or deactivate the rate smoothing in response to a detection of the trigger event.

13. The system of claim 1, wherein the controller circuit further comprises a trigger event detector configured to detect a trigger event from the physiologic parameter, and the rate smoothing module is configured to activate or deactivate the rate smoothing in response to a detection of the trigger event.

14. The system of claim 1, wherein the rate smoothing module is configured to select a stored rate smoothing algorithm in response to the detection of the predetermined state of the physiologic parameter.

15. The system of claim 1, wherein the rate smoothing module is configured to select a first rate smoothing percentage and a second rate smoothing percentage of the rate smoothing in response to the detection of the predetermined state of the physiologic parameter, the first rate smoothing percentage limiting a degree of pacing rate increase, the second rate smoothing percentage limiting a degree of pacing rate drop.

16. The system of claim 15, wherein the first rate smoothing percentage and the second rate smoothing percentage comprise different percentages.

17. The system of claim 15, wherein the rate smoothing module is configured to select the first rate smoothing percentage and the second rate smoothing percentage based on the activity level.

18. The system of claim 17, wherein the rate smoothing module is configured to set the first rate smoothing percentage and the second rate smoothing percentage to the same value in response to the activity level being below a predetermined activity level of the one or more predetermined activity levels.

19. The system of claim 17, wherein the rate smoothing module is configured to set the first rate smoothing percentage to a relatively large value and the second rate smoothing percentage to a relatively small value in response to the activity level exceeding a predetermined activity level of the one or more predetermined activity levels.

20. The system of claim 17, wherein the activity level detector is configured to determine the activity level falls within predetermined range of activity levels of the one or more predetermined activity levels.

21. The system of claim 1, wherein the rate smoothing module is configured to activate the rate smoothing or adjust the one or more rate smoothing parameters for a programmable time interval.

* * * * *